(12) United States Patent
Kazantsev et al.

(10) Patent No.: US 8,404,747 B2
(45) Date of Patent: Mar. 26, 2013

(54) COMPOSITIONS AND METHODS FOR MODULATING INTERACTION BETWEEN POLYPEPTIDES

(75) Inventors: Aleksey G. Kazantsev, Brookline, MA (US); Anne B. Young, Boston, MA (US); David E. Housman, Newton, MA (US); Steven Hersch, Boston, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 603 days.

(21) Appl. No.: 11/076,093

(22) Filed: Mar. 7, 2005

(65) Prior Publication Data
US 2005/0239833 A1 Oct. 27, 2005

Related U.S. Application Data

(60) Provisional application No. 60/550,748, filed on Mar. 5, 2004, provisional application No. 60/630,221, filed on Nov. 22, 2004, provisional application No. 60/630,230, filed on Nov. 22, 2004, provisional application No. 60/630,231, filed on (Continued)

(51) Int. Cl.
| *A61K 31/445* | (2006.01) |
| *A61K 31/4015* | (2006.01) |
| *A61K 31/21* | (2006.01) |
| *A61K 31/277* | (2006.01) |

(52) U.S. Cl. ................................. 514/601; 514/602
(58) Field of Classification Search ................ 514/485, 514/428, 424; 548/252, 567, 515, 428
See application file for complete search history.

(56) References Cited

U.S. PATENT DOCUMENTS

| 5,144,011 | A | | 9/1992 | Shen |
| 5,328,470 | A | | 7/1994 | Nabel |
| 5,994,392 | A | | 11/1999 | Shashoua |
| 5,994,398 | A | * | 11/1999 | John et al. ...................... 514/485 |
| 6,015,555 | A | | 1/2000 | Friden |
| 6,407,120 | B1 | | 6/2002 | Carpino |
| 2003/0008369 | A1 | * | 1/2003 | Windsor et al. ............... 435/194 |

FOREIGN PATENT DOCUMENTS

WO  WO 02/064618 A2 * 8/2002

OTHER PUBLICATIONS

Islam et al., "Sulphonamides derived from salicylic acid and its derivatives sulphamidosalicylanilides and related compounds." Proceedings of the Egyptian Academy of Sciences (1980); vol. 30; pp. 35-38.*
Barr et al., "The Reaction of 3-Chlorosulfonylbenzoyl Chloride with Amines." Journal of the American Chemical Society (1951); 73; 4131-3.*
Mohamed et al., "Synthesis of different types of chlorinated sulpohonamides with expected insecticidal and antimicrobial activities." Acta. Pharm. Jugosl.; 36 (1986); 301-310.*
Patani et al., "Bioisosterism: A Rational Approach in Drug Design." Chem. Rev. 1996:96;3147-3176.*
Trosko, "Mechanism of up-regulated gap junctional intercellular communication during chemoprevention and chemotherapy of cancer." Mutation Research 2000:480-481;219-229.*
Coleman et al., "Synthesis and characterization of novel analogs of conjugated bile acids containing reversed amide bonds." Journal of Lipid Research 1995:36;901-10.*
Bates et al., "Transgenic mice in the study of polyglutamine repeat expansion diseases" *Brain Pathol.* 8:699-714 (1998).
Chen et al.; "Gene therapy for brain tumors: regression of experimental gliomas by adenovirus-mediated gene transfer in vivo" *Proc. Natl. Acad. Sci. USA* 91:3054-3057 (1994).
Cruikshank et al., "A lipidated anti-Tat antibody enters living cells and blocks HIV-1 viral replication" *J. Acquired Immune Def Syndromes & Human Retrovirology* 14:193-203 (1997).
Czarnik "Encoding methods for combinatorial chemistry" *Curr. Opin. Chem. Bio.* 1:60-66 (1997).
Davies et al., "Formation of neuronal intranuclear inclusions underlies the neurological dysfunction in mice transgenic for the HD mutation" *Cell* 90:537-548 (1997).
DiFiglia et al., "Aggregation of huntingtin in neuronal intranuclear inclusions and dystrophic neurites in brain" *Science* 277:1990-1993 (1997).
Ferrante et al., "Therapeutic Effects of Mithramycin in R6/2 Transgenic HD Mice" *Soc. Neurosci. Abstr.* 28:725 (2002).
Gatter et al., "Transferrin receptors in human tissues: their distribution and possible clinical relevance" *J. Clin. Path.* 36:539-545 (1983).
Goldstein et al., "The blood-brain barrier" *Scientific American* 255:74-83 (1986).
Haynes et al., "Characterization of a monoclonal antibody (5E9) that defines a human cell surface antigen of cell activation" *J. Immunol.* 127:347-351 (1981).
Jackson et al., "Polyglutamine-expanded human huntingtin transgenes induce degeneration of Drosophila photoreceptor neurons" *Neuron* 21:633-642 (1998).
Kakizuka et al., "Protein precipitation: a common etiology in neurodegenerative disorders?" *Trends Genet.* 14:396-402 (1998).
Kazantsev et al., "Insoluble detergent-resistant aggregates form between pathological and nonpathological lengths of polyglutaime in mammalian cells" *Proc. Natl. Acad. Sci. USA* 96:11404-11409 (1999).
Lebman et al., "A Monoclonal Antibody That Detects Expression of Transferrin Receptor in Human Erythroid Precursor Cells" *Blood* 59(3):671-678 (1982).
Omary et al., "Human cell-surface glycoprotein with unusual properties" *Nature* 286:888-891 (1980).
Pardridge "Receptor-mediated peptide transport through the blood-brain barrier" *Endocrin. Rev.* 7:314-330 (1986).

(Continued)

*Primary Examiner* — Walter Webb
(74) *Attorney, Agent, or Firm* — Fish & Richardson P.C.

(57) ABSTRACT

The present invention is based, in part, on assays we conducted that revealed compounds that may be used to treat or prevent diseases characterized by an abnormal or undesirable association of one protein with another.

12 Claims, 1 Drawing Sheet

Related U.S. Application Data

Nov. 22, 2004, provisional application No. 60/630,252, filed on Nov. 22, 2004, provisional application No. 60/630,262, filed on Nov. 22, 2004, provisional application No. 60/630,264, filed on Nov. 22, 2004, provisional application No. 60/633,487, filed on Dec. 6, 2004.

(56) References Cited

OTHER PUBLICATIONS

Paulson "Protein fate in neurodegenerative proteinopathies: polyglutamine diseases join the (mis)fold" *Am. J. Hum. Genet.* 64:339-345 (1999).

Reddy et al:, "Recent advances in understanding the pathogenesis of Huntington's disease" *Trends Neurosci.* 22:248-255 (1999).

Rosinski et al., "A New Member of the Glutamine-rich Protein Gene Family Is Characterized by the Absence of Internal Repeats and the Androgen Control of Its Expression in the Submandibular Gland of Rats" *J. Biol. Chem.* 265(18):10709-10713 (1990).

Sutherland et al., "Ubiquitous cell-surface glycoprotein on tumor cells is proliferation-associated receptor for transferring" *Proc. Natl. Acad. Sci. USA* 78:4515-4519 (1981).

Zhuchenko et al., "Autosomal dominant cerebellar ataxia (SCA6) associated with small polyglutamine expansions in the alpha 1A-voltage-dependent calcium channel" *Nature* 15(1):62-69 (1997).

* cited by examiner

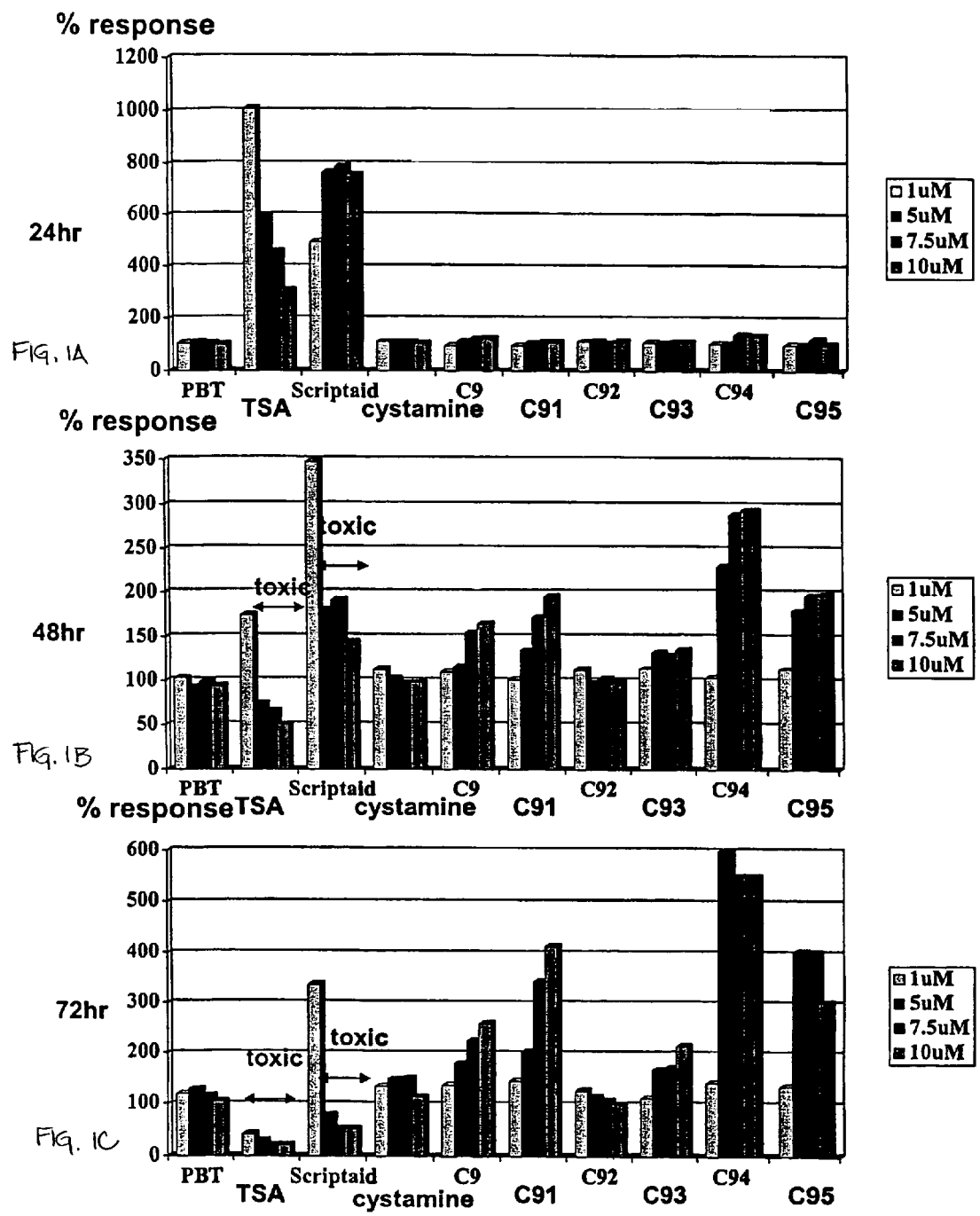

COMPOSITIONS AND METHODS FOR MODULATING INTERACTION BETWEEN POLYPEPTIDES

CROSS-REFERENCE TO RELATED APPLICATIONS

This application claims priority to U.S. application Ser. No. 60/550,748, filed on Mar. 5, 2004; and to U.S. Ser. No. 60/630,264, filed on Nov. 22, 2004. The entire contents of all of these provisional applications is hereby incorporated by reference in the present application.

TECHNICAL FIELD

This invention relates to compositions and methods for modulating the interaction between polypeptides. We describe exemplary compounds, which may be contained in pharmaceutical compositions, the screening methods by which they were discovered, and their use as therapeutic or prophylactic agents.

BACKGROUND

At least eight progressive neurodegenerative disorders are caused by an expansion of the naturally occurring CAG tract that encodes a polyglutamine (polyQ) repeat within the corresponding protein. These diseases include Huntington's disease (HD), spinal and bulbar muscular atrophy (SBMA; also known as Kennedy's disease), dentatorubral-pallidoluysian atrophy, spinocerebellar ataxia type 1 (SCA1), SCA2, SCA6, SCA7, and Machado-Joseph disease (MJD/SCA3)(Reddy et al., *Trends Neurosci.* 22:248-255, 1999). With the exception of SCA6 (CACNL1A4; Zhuchenko et al., *Nature* 15:62-69, 1997), which is characterized by a minimal repeat expansion, affected individuals typically show a similar range of repeat expansion above ~35 repeats (Kakizuka et al., *Trends Genet.* 14:396-402, 1998).

Of the diseases listed above, HD has arguably been studied the most intensely, and one of the tools extensively used in those studies is a transgenic mouse model. The neurons within mice transgenic for exon 1 of huntingtin are marked by intranuclear inclusions that contain huntingtin and ubiquitin (Bates et al., *Brain Pathol.* 8:699-714, 1998; and Paulson et al., *Am. J. Hum. Genet.* 64:339-345, 1999). These inclusions indicate that protein misfolding and aggregation mediate neuronal pathogenesis (Davies et al., *Cell* 90:537-548, 1997). Moreover, nuclear inclusions have been observed in the affected regions of brains of patients diagnosed as having a polyQ-associated disease (Kakizuka et al., *Trends Genet.* 14:396-402, 1998; DiFiglia et al., *Science* 277:1990-1993, 1997; Bates et al., *Brain Pathol.* 8:699-714, 1998; and Paulson et al., *Am. J. Hum. Genet.* 64:339-345, 1999).

SUMMARY

The present invention is based, in part, on our discovery of compounds that can be used to treat or prevent diseases that are believed to be caused by an aberrant association of proteins within a cell. The compounds can, for example, be used in the treatment or prevention of neurological disorders in which polypeptides form aggregates or other complexes within cells. The compounds were identified in our screening assays based on their ability to inhibit or facilitate the association of one protein with another. While these compounds may mediate the undesirable association that occurs between polypeptides in the course of certain diseases, whether by modulating that association or an upstream or downstream event, the invention is not limited to compounds that exert their effect on the disease process by any particular mechanism. While we tend to use the term "compound(s)", we may also use terms like "agent(s)" to refer to the molecules described herein.

We have placed each of the compounds we identified into one of five categories. The compounds in the first four categories are represented by Formulas I-IV. The compounds in the fifth category are represented by Formulas V(a)-V(u). The invention encompasses these compounds in, for example, a substantially pure form, as well as various compositions containing one or more of them (e.g., pharmaceutical formulations) and methods of using them.

Formula I is:

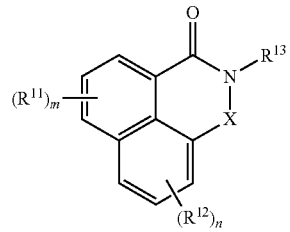

Formula I

In Formula I, X can be C(O) or a bond; each $R^{11}$ and $R^{12}$ can be, independently, halo (e.g., bromo), nitro, amino, hydroxy, alkoxy, alkyl, alkenyl, alkynyl, cyclyl, heterocyclyl, aryl, arylalkyl, heteroaryl, or heteroarylalkyl, $NR^{15}C(O)R^{14}$, or $C(O)NR^{15}R^{16}$; each of which can be optionally substituted with 1-4 $R^{17}$; $R^{13}$ can be H, alkyl, alkenyl, alkynyl, amino, hydroxy, aryl, arylalkyl, arylamino, heterocyclyl, heterocyclylalkyl, heteroaryl, heteroarylalkyl, cyclyl, cyclylalkyl, aminoalkyl, hydroxyalkyl, or alkoxyalkyl; each of which can be optionally substituted with 1-4 $R^{18}$; $R^{14}$ can be H, alkyl, alkenyl, alkynyl, cyclyl, heterocyclyl, aryl, or heteroaryl; each of $R^{15}$ and $R^{16}$ can be, independently, H, hydroxy, alkoxy, alkyl, alkenyl, alkynyl, cyclyl, heterocyclyl, aryl, arylalkyl, heteroaryl, or heteroarylalkyl; each $R^{17}$ can be, independently, halo (e.g., bromo), alkyl, alkoxy, or hydroxy; each $R^{18}$ can be, independently, halo (e.g., bromo), alkyl, amino, hydroxy, $C(O)NR^{15}R^{16}$, $NR^{15}C(O)R^{14}$, or hydroxyalkyl; and m and n are each, independently, an integer from 0 to 3. The compositions of the invention can include a compound of Formula I, with the proviso that the compound is not Scriptaid (6-(1,3-Dioxo-1H,3H-benzo[de]isoquinolin-2-yl)-N-hydroxyhexanamide), which is a histone deacetylase (HDAc) inhibitor; Mitonafide (5-nitro-2-(2-dimethylaminoethyl)-benzo(de)isoquinoline-1,3-dione), which is an intercalating agent; or Amonafide (1H-Benz[de]isoquinoline-1,3(2H)-dione, 5-amino-2-[2-(dimethylamino)ethyl]-(9CI), which is also an intercalating agent. The proviso can extend to 5-amino-2-(2-diethylamino-ethyl)-benzo[de]isoquinoline-1,3-dione (see Table 1). The excluded compounds may be encompassed by the invention when newly formulated in a particular manner (e.g., as one of the pharmaceutical formulations set out below) or as part of a kit or as packaged for storage, shipment, or sale. Of course, their use in treating or preventing a disease characterized by an unwanted association of proteins is also new. Specific compounds that conform to Formula I are shown in Table 1.

Formula II is:

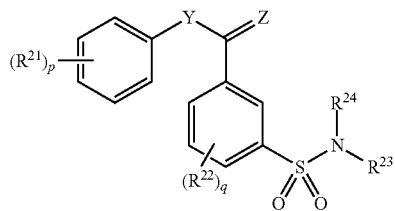

Formula II

In Formula II, Z can be O or S; Y can be O, $NR^{25}$ or $CR^{26}R^{27}$; each of $R^{21}$ and $R^{22}$ can be independently halo (e.g., bromo), hydroxy, nitro, cyano, amino, amido, or alkyl; $R^{23}$ can be alkyl, cyclyl, aryl, heteroaryl, cyclylalkyl, arylalkyl, or heteroarylalkyl, or can be taken together with $R^{24}$ and the nitrogen to which it is attached to form a ring where $R^{23}$ is optionally substituted with 1-3 $R^{28}$. $R^{24}$ can be H or alkyl, or can be taken together with $R^{23}$ and the nitrogen to which it is attached to form a ring where $R^{24}$ is optionally substituted with 1-3 $R^{28}$; $R^{25}$ can be H or alkyl; each of $R^{26}$ and $R^{27}$ can be, independently, H or alkyl; each $R^{28}$ can be independently halo (e.g., bromo), hydroxy, nitro, cyano, amino, amido, or alkyl; and each p and q can be, independently, an integer from 0-4. Specific compounds that conform to Formula II are shown in Table II.

Formula III is:

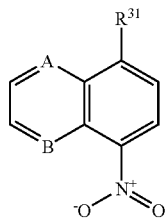

Formula III

In Formula III, A can be N or $CR^{32}$; B can be N or CH; $R^{31}$ can be H or $NR^{33}R^{34}$; $R^{31}$ can be optionally substituted with 1-3 $R^{35}$; $R^{32}$ can be H or $NR^{33}R^{34}$; $R^{32}$ can be optionally substituted with 1-3 $R^{35}$; $R^{33}$ can be H, alkyl, or taken together with $R^{34}$ and the nitrogen to which it is attached forms a heterocyclyl ring; $R^{34}$ can be H, alkyl, arylalkyl, heteroarylalkyl, cyclylalkyl, heterocyclylalkyl or taken together with $R^{33}$ and the nitrogen to which it is attached to form a heterocyclyl ring; each $R^{35}$ can be, independently, halo (e.g., bromo), hydroxy, amino, nitro, alkyl, aryl, arylacyl, arylalkyl, heteroaryl, heteroarylacyl, heteroarylalkyl; cyclylacyl; heterocyclylacyl; or alkylacyl; $R^{35}$ can be optionally substituted with 1-4 $R^{36}$; each $R^{36}$ can be, independently, halo (e.g., bromo), alkyl, nitro, amino or hydroxy. Specific compounds that conform to Formula III are shown in Table 3.

Formula IV is:

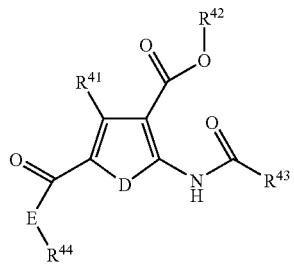

Formula IV

In Formula IV, D can be O, S, or NH; E can be O or NH; $R^{41}$ can be halo (e.g., bromo), alkyl, amino, hydroxy, alkoxy; $R^{42}$ can be alkyl, arylalkyl, cyclyl, or cyclylalkyl; $R^{43}$ can be alkyl, alkenyl, alkynyl, aryl, arylalkyl, heteroaryl, heteroarylalkyl, cyclyl, cyclylalkyl, heterocyclyl, or heterocyclylalkyl, where $R^{43}$ is optionally substituted with 1-4 $R^{45}$; $R^{44}$ can be alkyl, cyclyl, cyclylalkyl, aryl, arylalkyl, heteroaryl, heteroarylalkyl, heterocyclyl, or heterocyclylalkyl, where $R^{44}$ is optionally substituted with 1-4 $R^{46}$; each $R^{45}$ can be independently halo (e.g., bromo), alkyl, amino, amido, hydroxy, alkoxy, nitro, cyano, thio, alkylthio, sulfonyl, or sulfonamidyl; and each $R^{46}$ can be independently halo (e.g., bromo), alkyl, amino, amido, hydroxy, alkoxy, nitro, cyano, thio, alkylthio, sulfonyl, or sulfonamidyl. Specific compounds that conform to Formula IV are shown in Table 4.

Each of the variables designated by, for example, R, X, Y, m, and n in any of the formulas disclosed herein can be selected independently. While we tend to use the term "compound(s)", we may also use terms like "agent(s)" to refer to the molecules described herein.

The compounds of Formulas V(a) through V(u) are shown in Table 5.

The invention also encompasses pharmaceutically acceptable salts or solvates of a compound of any of Formulas I-IV or V(a)-V(u), and prodrugs, metabolites, structural analogs, and other pharmaceutically useful variants thereof. These other variants may be, for example, a complex containing the compound and a targeting moiety, as described further below, or a detectable marker (e.g., the compound may be joined to a fluorescent compound or may incorporate a radioactive isotope). When in the form of a prodrug, a compound may be modified in vivo (e.g., intracellularly) after being administered to a patient or to a cell in culture. The modified compound (i.e., the processed prodrug) may be identical to a compound described herein and will be biologically active or have enough activity to be clinically beneficial. The same is true of a metabolite; a given compound may be modified within a cell and yet retain sufficient biological activity to be clinically useful.

Packaged products (e.g., sterile containers containing one or more of the compounds described herein and packaged for storage, shipment, or sale) and kits, including at least one compound of the invention and instructions for use, are also within the scope of the invention.

In one aspect, the invention features substantially pure preparations of the compounds described herein or combinations thereof. A naturally occurring compound is substantially pure when it is separated to some degree from the compound(s) or other entities (e.g., proteins, fats, or minerals) it is associated with in nature. For example, a naturally occurring compound described herein is substantially pure when it has been separated from 50%, 60%, 70%, 75%, 80%, 85%, 90%, 95%, 96%, 97%, 98%, 99% or more of the compound(s) or other moieties it is associated with in nature. While the compounds of the invention may be naturally occurring and may be purified using conventional techniques, they may also be non-naturally occurring and may be synthesized (naturally occurring compounds can be synthesized as well). Compounds prepared by chemical synthesis are substantially pure, as are compounds that have been separated from a library of chemical compounds. A substantially pure compound may be one that is separated from all the other members of the compound library or it may be one that has been separated to a limited extent (e.g., it may remain associated with a limited number (e.g., 1, 2, 3, 4, or 5-10) of other members of the library). A compound library is not a pharmaceutical or therapeutic composition.

Regardless of their original source or the manner in which they are obtained, the compounds of the invention can be formulated in accordance with their use. For example, the compounds can be formulated within compositions for application to cells in tissue culture or for administration to a patient. For example, the compounds can be mixed with a sterile, pharmaceutically acceptable diluent (such as normal saline). As noted below, and as known in the art, the type of diluent can vary depending upon the intended route of administration. The resulting compositions can include additional agents, such as preservatives. The compounds may also be applied to a surface of a device (e.g., a catheter) or contained within a pump, patch, or other drug delivery device.

Whether in cell culture or in vivo, when proteins associate (either on the cell surface, within the cell, or following secretion from the cell), they may do so in a variety of ways. When a compound of the invention interferes with the way one protein would otherwise interact with another (i.e., the way proteins would associate in the absence of the compound), the compound may mediate, for example, aggregation, dimerization, multimerization, accumulation or participation within complexes, or any other physiologically significant association between proteins.

We may refer to the protein that is affected by the compound as a target protein. The target protein may be the protein most directly involved with, or associated with, the disease process. For example, the target protein can be an Aβ protein found in the plaques associated with Alzheimer's disease, a tau protein within a neurofibrillary tangle, the Huntingtin protein that aggregates in Huntington's disease, or oncogenic proteins such as fos and jun. We may refer to these target proteins as primary target proteins. Alternatively, the target protein can be a protein that is active upstream or downstream in a biochemical pathway in which the primary target protein is active. We may refer to these target proteins as secondary target proteins. For example, the secondary target protein can be a transcription factor that facilitates expression of a gene encoding a primary target protein. The secondary target protein could also be a protein whose activity changes upon interacting with the primary target protein. For example, where the primary target protein is an enzyme, the secondary target protein can be that enzyme's substrate. Alternatively, the secondary target protein could be a kinase that activates the primary target protein by phosphorylating it. These scenarios are meant to describe the manner in which the compounds of the invention may exert their effect on protein-protein interaction within a cell, but the invention is not so limited. The invention encompasses compounds according to the formulas described herein, compositions containing them (e.g., pharmaceutical formulations), and methods of using them regardless of the mechanism by which they work. The target proteins may contain stretches of consecutive glutamine residues or glutamine-rich regions (e.g., regions containing a sufficient number of glutamine residues that protein behavior is adversely affected), but the compounds of the invention may mediate or modulate association between other polypeptides as well.

The target proteins, whether primary or secondary, can be identical or non-identical (e.g., a compound of the invention can facilitate or inhibit the dimerization of proteins in a homodimer or heterodimer or may facilitate or inhibit the aggregation of one Huntingtin protein to another). Some of the target proteins affected by the compounds of the present invention may contain stretches of consecutive glutamine residues or glutamine-rich regions, but the invention is not so limited; the compounds of the invention may mediate association between other proteins (e.g., the secondary target proteins described above) or between primary and secondary proteins. The compounds of the invention may be useful in the treatment of aggregation-associated diseases by affecting the disease mechanism in another way (e.g., by facilitating degradation of a target protein).

"PolyQ-containing" polypeptides include a number of consecutive glutamine residues, which may be described in the art as homopolymeric polyQ regions, while "glutamine-rich" polypeptides include other (non-glutamine) amino acid residues interspersed within glutamine residues. The transcriptional factor CBP, the yeast prion proteins RNQ1 and Sup35, Sp1, and the TAFII130 subunit of the transcription factor TFIID are examples of proteins that include glutamine-rich regions. While the number of consecutive glutamine residues may be quite low (e.g., as few as 3-10 (e.g., five)), polyQ-containing polypeptides typically have about 26 or more consecutive amino acid residues (e.g., 28, 30, 33, 34, 35, 36, 37, 40, 42, 47, 50, 52, 60, 65, 70, 72, 75, 80, 85, 95, 100, 103, 104, 110, 119, 120, 130, 140, 144, 151, 160, 170, 180, 190, 191, 195, 200, 210, 230, 250, 270 or 300 consecutive glutamine residues). For example, a glutamine-rich polypeptide can have at least 32 consecutive glutamine residues. Polypeptides having such a region of consecutive glutamine residues may also be referred to as having an "extended" polyglutamine region. PolyQ-containing or glutamine-rich polypeptides can be naturally occurring polypeptides such as the huntingtin protein, atrophin-1, ataxin-1, ataxin-2, ataxin-3, the α1a-voltage dependent calcium channel, ataxin-7, the androgen receptor, alpha-, beta-, and gamma-synucleins, polypeptides involved in amyloidosis, such as those containing immunoglobulin light chains, amyloid-associated proteins (e.g., alpha1-antichymotrypsin, apolipoprotein E (apoE), SP-40, and ubiquitin), mutant transthyretin, beta2 microglobulin, beta2 amyloid protein, and the prion proteins. Other proteins that may be affected by the compounds of the present invention include those that form complexes with cellular receptors (e.g., a cell surface or nuclear receptor) or that participate in dimers or multimers (e.g., transcription factors). Accordingly, the invention features compounds that inhibit the aggregation of (or other undesirable association between) any one or more of the aforementioned polypeptides, and methods of treating a subject in which any one of those polypeptides associate, or fail to associate, to an extent that cellular function is disrupted and a disease state results (e.g., a subject having immunoglobulin light chain amyloidosis, HD, Parkinson's disease, adult-onset diabetes, cirrhosis, emphysema, or a prion disease, such as Creutzfeldt-Jakob disease). For example, one or more of the compounds of the invention may block nuclear aggregation of androgen receptors. Accordingly, the invention features compounds that inhibit the aggregation of (or other undesirable association between) any one of the aforementioned polypeptides and methods of treating a subject in which any one of those polypeptides associate, or fail to associate, to an extent that cellular function is disrupted and a disease state results.

In addition to determining the effect of a compound on polypeptide association (and, in animal models or clinical trials, the effect of a compound on the signs and symptoms of a disease), the assays or screens can include a step in which one determines cellular toxicity. One can also generate a dose response profile of putative assay hits and record the results in a screening database (which is also within the scope of the present invention).

In specific embodiments, the compositions of the present invention can be administered to a subject having immunoglobulin light chain amyloidosis, HD, Parkinson's disease, adult-onset diabetes, cirrhosis (e.g., cirrhosis of the liver), emphysema, or a prion disease, such as Creutzfeldt-Jakob disease. Other conditions that can be treated or prevented with one or more of the compounds of the present invention include amyotrophic lateral sclerosis, dentatorubral pallidoluysian atrophy, spinal bulbar muscular atrophy (SBMA; also known as Kennedy's disease), any of the several types of spinocerebellar ataxias (e.g., SCA1, SCA2, SCA6, SCA7 and Machado-Joseph disease (MJD/SCA3)), dentatorubral-pallidoluysian atrophy, and disorders in which polyglutamine-containing transcription factors or coactivators are undesirably active (e.g., disorders associated with homodimerization of jun or hexamerization of p53). For example, a subject may have been diagnosed as having, or at risk for developing, a carcinoma (e.g., breast cancer), amyloidosis, a myeloma, kuru, a neuroblastoma, cystic fibrosis, an alpha-1-antitrypsin deficiency disease, or a disorder with a similar underlying cellular basis (i.e., an association with undesirable (e.g., excessive or insufficient) protein-protein aggregation, dimerization, or other interaction).

Therapeutic methods featured in the invention can include the step of identifying a subject in need of treatment. The subject can be identified by, for example, a health care professional (e.g., a physician) on the basis of subjective or objective information (e.g., based on comments from the subject, a physical examination, and/or on measurable parameters (i.e., diagnostic tests)). Subjects who are treated with the compounds featured in the invention may have been diagnosed with any disease characterized by aberrant or undesirable association between proteins, whether that association occurs to a greater or lesser extent than is normal (in, e.g., a healthy patient) or desirable. Alternatively, the subject may be at risk for developing these disorders. For example, a subject may have a family history or a genetic mutation or element (e.g., an expanded trinucleotide repeat) that contributes to the development of disease. Human subjects, in consult with their physicians and/or other health care professionals, can decide whether their risk is great enough to undergo preventative care (as is the case for any prophylactic treatment or procedure). While the subjects of the preventative and/or therapeutic regimes described herein may be human, the compounds and compositions of the invention can also be administered to non-human subjects (e.g., domesticated animals (such as a dog or cat), livestock (e.g., a cow, pig, sheep, goat, or horse), or animals kept in captivity (e.g., any of the large cats, non-human primates, zebra, giraffes, elephants, and the like kept in zoos, parks, or preserves)).

The prophylactic and therapeutic methods can be carried out by administering to the subject a pharmaceutical composition containing a therapeutically effective amount of one or more of the compounds described herein. While a single compound may be effective, the invention is not so limited. A subject can be treated with multiple compounds, administered simultaneously or sequentially (i.e., before or after a compound of the present invention). For example, a subject can be treated with one or more of the compounds described herein and, optionally, a chemotherapeutic agent, an analgesic, a bronchodilator, levodopa or a similar medication, haloperidol, or risperdone. In other embodiments, the "second" agent can be a vitamin, mineral, nucleic acid (e.g., an antisense oligonucleotide or siRNA), a therapeutic protein (e.g., a peptide), including therapeutic antibodies or antigen-binding portions thereof, or an anti-inflammatory agent. Compositions containing a compound of the invention and a second agent, as described herein, are also within the scope of the present invention.

The combination therapy will, of course, depend on the disorder being treated. Where a compound of the invention is administered to treat a patient with a cancer, it may be combined with a known chemotherapeutic agent used to treat that type of cancer; where a compound of the invention is administered to treat a patient with Parkinson's disease, it may be combined with a medication to increase dopamine levels in the brain; and so forth.

Compounds that mediate association between proteins can also be used to diagnose diseases characterized by protein aggregation (or, as noted above, other undesirable interaction (e.g., dimerization or complex formation)). These methods can be carried out by providing a biological sample from a patient suspected of having a disease associated with an abnormal or undesirable association between proteins; exposing the sample to a compound of the invention; and determining whether the compound modulates the association of proteins within the sample. The compound can be one that is known to interact directly with a primary target or one that modulates protein-protein interaction by acting upstream or downstream from the primary target. The compound can also be one that is known to interact with proteins in the context of the suspected disease. For example, a compound that is known to inhibit the aggregation of Huntingtin can be used to diagnose a patient suspected of having HD. The sample will be exposed to the compound for a time and under conditions (e.g., physiological conditions of temperature and pH) sufficient to permit the compound to affect proteins within the sample (e.g., Huntingtin, tau, or A$\beta$ proteins within cells within the sample). The diagnostic methods can be carried out before, after, or in conjunction with other diagnostic tests, and their results can inform the subject's treatment regime. For example, where a compound is found to modulate the aggregation of Huntingtin proteins in a sample obtained from a patient suspected of having HD, that compound may then be used to treat the patient.

With respect to "aggregation associated" diseases, the predominant theory is that the protein rich aggregates that form within cells are deleterious. However, a contrary theory holds that aggregation is a cellular defense mechanism; harmful proteins aggregate, forming large inclusions that are targeted by, and slowly degraded by, cellular enzymes. If the latter theory proves true to any extent, compounds that facilitate aggregation will be efficacious therapeutic agents. If, instead, the former theory emerges, compounds that inhibit protein-protein aggregation will be efficacious therapeutic agents. In either event, all of the present compounds can be formulated for use in cell culture and/or in vivo administration and supplied as reagents for research, as described herein. For example, the compounds can be used to generate cellular or animal models of the diseases described above, and the cellular or animal models can include a step of determining a dose response profile and cellular toxicity.

Compounds that can mediate association between proteins (e.g., polyglutamine-containing polypeptides) can be identified by the screening methods of the invention. As noted above, these compounds may modulate interaction between proteins in different ways; the screening methods of the invention are not limited to those that identify compounds that work by any particular mechanism, nor are the compounds so limited. In some embodiments, the compounds may bind to polypeptides prone to aggregate. In other embodiments, the compounds may act as transcriptional repressors or enhancers (in this scenario, a compound stimulates or inhibits transcription of a gene encoding a polypeptide that aggregates or that is prone to aberrant aggregation; by virtue of, respectively, increasing or decreasing the amount of the protein within the cell, the protein becomes more or less likely to aggregate). The compounds of the invention may also (or may alternatively) affect protein or RNA stability, thereby affecting polypeptide accumulation within a cell (more stable RNAs or proteins being more prone to associate to an undesirable extent). The compounds may also modulate the post-translational processing of a protein (improperly processed proteins being less prone to associate to an undesirable extent). For example, a compound may interact with a kinase, phosphatase, methyl transferase, ubiquitinase, protease (e.g., an aspartyl protease such as cathepsin D or BACE-1 or BACE-2), polymerase (e.g., PARP-1), or other modifying enzyme. Interruption of post-translational processing events may alter the ability of a protein to aggregate, or may alter the stability of a protein, which in turn may affect the accumulation of polypeptide aggregates or other complexes as discussed above. In yet other embodiments, a compound may interact with (e.g., bind to) a protein that mediates protein folding, such as a chaperone protein (e.g., a stress protein such as a heat shock protein (hsp; e.g., a human hsp or an hsp expressed within a human cell)). Interaction of the compound with the chaperone can stabilize, or otherwise modify, its activity, thereby modifying protein folding in the cell and the tendency of proteins to aggregate. Yet other compounds may modulate aggregation by rescuing proteasome dysfunction. Representative compounds are shown in Tables 1-5.

Other features and advantages of the invention will be apparent from the accompanying drawings and description, and from the claims.

BRIEF DESCRIPTION OF THE DRAWINGS

FIGS. 1A-1C. FIG. 1A is a bar graph showing luciferase expression in Sp1-luc/111Q striatum double knock-in cells following treatment with different compounds, as indicated. Fluorescence was measured 24 hours after addition of compound. FIG. 1B is a bar graph as described in FIG. 1A. Fluorescence was measured 48 hours after addition of compound. FIG. 1C is a bar graph as described in FIG. 1A. Fluorescence was measured 72 hours after addition of compound.

DETAILED DESCRIPTION

Small molecule-based therapeutics have provided the means to successfully treat many diseases, and the identification of pharmacological agents that can reverse, block, or delay disease-linked processes in model systems is critical to the development of effective treatments for the diseases described herein. Our assays employ in vitro model systems that recapitulate key features of disease pathology and that are adaptable to high throughput screening against a large collection of chemical compounds.

Using our assays and screens, we have identified compounds we believe are capable of modulating (either directly or indirectly) the association of polypeptides including those that, when abnormally expressed or associated, cause pathological disorders such as Parkinson's disease, Huntington's disease, and the other diseases referred to herein (we tend to use the term "disease" to refer to any disorder, unwanted condition, or syndrome). The compounds described herein can be used to modulate (e.g., inhibit) the aggregation of polypeptides, such as polyQ-containing polypeptides that are associated with pathological disorders, as well as non-naturally occurring polypeptides (e.g., polyQ-containing polypeptides that are used in disease models, such as models of HD). Before describing exemplary compounds, we provide exemplary assays that can be used to test (or further test) those compounds as well as to identify other compounds or moieties, such as proteins (e.g., antibodies) and nucleic acids (e.g., oligonucleotides or molecules that mediate RNAi (e.g., siRNAs or shRNAs)) useful in the diagnosis, prevention, or treatment of a disease characterized by an abnormal association of one protein with another.

Assays: A variety of assays are available to identify, test and/or monitor the effect of a compound or other moiety on protein association (e.g., the aggregation of polyglutamine repeat-containing polypeptides). In one assay, for example, a cell expresses a fusion protein that contains a detectable label such as a fluorescent or luminescent polypeptide (e.g., a fusion protein that contains a detectable label and a glutamine-rich polypeptide). The polypeptide can be one that naturally fluoresces or a non-fluorescent polypeptide that is labeled with a tag (e.g., an enzyme, fluorescent, luminescent (e.g., bioluminescent), or otherwise detectable tag). Examples of suitable enzymes include horseradish peroxidase, alkaline phosphatase, β-galactosidase, and acetylcholinesterase; examples of suitable fluorescent materials include umbelliferone, fluorescein, fluorescein isothiocyanate, rhodamine, dichlorotriazinylamine fluorescein, dansyl chloride, phycoerythrin, green fluorescent protein, and blue fluorescent protein; an example of a luminescent material is luminol; examples of bioluminescent materials include luciferase, luciferin, and aequorin; and examples of suitable radioactive materials include $^{125}I$, $^{131}I$, $^{35}S$, $^{32}P$, and $^{3}H$. These labels and tags may be used not only to label substrates useful in the assays, but also to label the compounds identified therein. The coupling of a label to the aggregation-disposed polypeptide or a compound that affects such a peptide can be carried out by chemical methods known in the art.

In an exemplary assay, the cell is exposed to a compound (e.g., incubated with the compound), and the signal from the detectable label can be evaluated. If a fluorescent tag (e.g., GFP, EGFP, BFP, etc. . . . ) is used, the fluorescent aggregates can be detected and quantified by fluorescent microscopy. Aggregate-positive cells and the effects of compounds on protein aggregation can be detected by any method known in the art (e.g., using a fluorometer or by fluorescence-activated cell sorting). To facilitate the reading, cells containing aggregates and soluble fluorescent polypeptides can be incubated for an extended time. Prolonged incubation promotes cellular degradation of soluble polyQ-containing proteins, leaving intact aggregates that are resistant to degradation. Cells typically degrade soluble polypeptides rapidly. For example, PC12 cells usually clear soluble polyQ in about 24 hours, whereas intracellular aggregates are retained much longer. An increase in the intensity of the detectable label (e.g., an increase in fluorescence) following incubation of the cell with the compound indicates that the compound promotes interaction (e.g., aggregation) between polypeptides (e.g., glutamine-rich polypeptides). Conversely, a decrease in the intensity of the detectable label indicates that the compound inhibits protein interaction.

A detectable label can be a label detected by indirect methods, as by an antibody detection assay. For example, the aggregation-disposed protein can be fused to an N-terminal amino acid sequence consisting of 5-35 (e.g., 5, 8, 10, 12, 15, 18, 20, 23, 27, 29, 31, or 35) amino acid residues from any existing protein or of any random sequence. The N-terminal amino acid sequence can also be the FLAG-tag sequence (MYKDDDDK (SEQ ID NO:1)). Alternatively, the tag can be a histidine (His) tag, influenza hemagglutinin (HA) tag, Myc tag, VSV-G tag, or thioredoxin (Trx) tag. Other detectable protein fusion tags include beta-galactosidase, beta-glucuronidase, glutathione-S-transferase (GST), luciferase, horseradish peroxidase (HRP) and chloramphenicol acetyltransferase (CAT). When a non-fluorescent tag is used, association of aggregation-disposed polypeptides can be assessed by exposing the cell to antibodies that specifically bind the non-fluorescent polypeptide. Of course, the antibodies that specifically bind the non-fluorescent polypeptide can be fluorescently labeled. In any event, while fluorescence can be measured with a device, such as a fluorimeter, it is also possible to detect changes in fluorescence by viewing a labeled cell directly under the microscope. Changes in the size of protein aggregates can be readily apparent to the eye and can be detected by automated systems.

To most accurately assess a compound, the signal generated by the detectable label (e.g., fluorescent polypeptide) can be assessed just after the cell has been exposed to the compound (i.e., before any significant incubation has occurred) as well as after the period of incubation. When the method is carried out in this way, the first reading will more accurately reflect the background signal intensity by taking into account any fluorescence emitted by the compound per se. Of course, less accurate measurements can be obtained in other ways (e.g., by assessing background signal before the compound is added to the cell). In this method, as well as the others described herein, the compound can be virtually any substance (e.g., the compound can be a biological molecule, such as a polypeptide expressed in the cell, a chemical compound, or a small molecule). Libraries that encode or contain candidate compounds are available to those of ordinary skill in the art through charitable sources (e.g., ChemBridge Corporation (San Diego, Calif.) (which provides useful information about chemical libraries on the worldwide web)) and commercial suppliers.

The cells that can be used in the methods and assays described herein can be mammalian cells (e.g., the cell of a rodent, non-human primate, or human) or yeast cells (of any strain). Regardless of the cell type used, the recombinant proteins (e.g., fusion proteins) they express can be placed under the control of an inducible promoter. Many useful inducible promoters are known in the art. For example, in the event yeast cells are employed, the fusion protein can be placed under the control of a Gal1 promoter.

In one assay, a compound that modulates (e.g., inhibits or promotes) the interaction (e.g., aggregation) of polypeptides, such as glutamine-rich polypeptides, can be identified by obtaining a cell that expresses a fusion protein that includes the polypeptide (e.g., a glutamine-rich polypeptide, whether naturally or non-naturally occurring), exposing the cell to the compound, and assessing the growth rate of the cell. An increase in the growth rate of the cell can indicate that the compound favorably modulates (e.g., inhibits) the interaction of the polypeptides. Conversely, suppression of growth can indicate that the compound stimulates or promotes the interaction of the polypeptides and that interaction is deleterious to the cell. The significance of the results may differ depending upon the disease model (e.g., a model of cancer; or an assay conducted with tumor cells in culture or in vivo). The polypeptides whose aggregation is in question can be identical to one another or they may differ from one another.

Assays can be used to identify a gene product that mediates interaction of aggregation-disposed polypeptides or other target proteins (i.e., a gene product that, possibly in concert with other gene products, functions to either promote or inhibit the association of polypeptides, including glutamine-rich polypeptides). Gene products, which serve as targets for therapeutic agents, can be identified in assays in which fluorescence, cell growth, or both, are assessed. For example, a gene product that mediates the interaction between aggregation-disposed polypeptides can be identified by obtaining a mutant yeast cell that expresses an aggregation-disposed polypeptide and assessing the rate of growth of the cell. An increase in the rate of growth, relative to that of a wild type yeast cell that expresses the aggregation-disposed polypeptide indicates that the gene product that is mutant in the yeast cell is a gene product that mediates aggregation of the aggregation-disposed polypeptides. Alternatively, where a fluorescence-based assay is used, a gene product that mediates interaction of aggregation-disposed polypeptides can be identified by obtaining a mutant yeast cell that expresses fusion protein that includes an aggregation-disposed polypeptide and a fluorescent polypeptide, exposing the cell to the compound, incubating the cell with the compound, and assessing the fluorescence emitted by the fluorescent polypeptide. A decrease in fluorescence, relative to that of a wild type yeast cell that expresses the aggregation-disposed polypeptide, indicates that the gene product that is mutant in the yeast cell is a gene product that mediates aggregation of glutamine-rich polypeptides.

Another method that can be used to identify a target for a therapeutic agent is carried out by obtaining cells that express a fusion protein that includes a polypeptide (e.g., a polypeptide prone to aggregation (e.g., a glutamine-rich polypeptide, perhaps in the context of a disease process) or other target protein), transfecting the cells with an expression library of mammalian genes, and assessing the growth of the cells. An alteration in the growth of a cell (among those transfected and relative to non-transfected cells) indicates that that cell has been transfected with a mammalian gene that mediates aggregation of the polypeptide (e.g., the glutamine-rich polypeptide). Therefore, the gene, or the gene's product, is a target for a therapeutic agent that mediates the aggregation of glutamine-rich polypeptides. Here again, the method can be fluorescence-based, in which case the cell would express a fusion protein that includes a glutamine-rich polypeptide and a fluorescent polypeptide, and fluorescent emission, rather than cell growth, would be assessed.

Cultured cells, whether labeled or exposed to a detectably-labeled compound or not, can also be used to carry out toxicity studies of the compounds described herein and others (e.g., others identified by the assays of the invention). Using such studies, we determined that none of compounds C1-C8 are cytotoxic. Compounds that undesirably block interactions between proteins (e.g., transcription factors) are very likely to affect cell viability.

For use in the screening methods, both naturally occurring and non-naturally occurring aggregation-disposed polypeptides can be produced recombinantly. Recombinant methods can be used to fuse other proteins (e.g., heterologous proteins) to the aggregation-disposed polypeptides. For example, a glutamine-rich polypeptide such as huntingtin, can be fused to an antigenic tag, such as c-myc or FLAG-tag, or a proteinaceous label such as a green fluorescent protein (GFP, which term includes enhanced GFP, or "EGFP"). Such fusion proteins, nucleic acid sequences encoding them, and expression vectors useful in mediating expression are also within the scope of the present invention. The cell in which the recombinant polypeptide is produced can be used directly in the methods of the invention, or the recombinant polypeptide can be purified from the culture medium or from a lysate of the cells. Cells that include an association-disposed polypeptide and, optionally, a compound disclosed herein (e.g., a compound of any of Tables 1-5 or a salt, solvate, biologically active variant or other analog thereof) are within the scope of the present invention, as are arrays of such cells.

Variants of the aggregation-disposed polypeptides can also be targets of the compounds of the invention, or used in the assays described herein. Variants can be prepared by substituting selected amino acid residues in the polypeptides. A variant of an aggregation-disposed polypeptide includes a polypeptide that has high sequence identity (e.g., 60, 70, 80, 90, 95, 96, 97, 98, or 99%) to an aggregation-disposed polypeptide and retains the ability to aggregate.

Isolated nucleic acid molecules that encode naturally occurring, aggregation-disposed polypeptides, variants thereof, or non-naturally occurring aggregation-disposed polypeptides are useful in the methods of the invention and in the assays described herein. Naturally occurring nucleic acid sequences that encode aggregation-disposed polypeptides are well known in the art and can be obtained, for example, from GENBANK™. The nucleic acid triplet that encodes the amino acid glutamine can be either CAA or CAG. The CAA or CAG codons need not be present in equal numbers and need not form a repeating pattern.

Typically, expressing an aggregation-disposed polypeptide in a cell involves inserting an aggregation-disposed polypeptide coding sequence into a vector, where it is operably linked to one or more expression control sequences. The need for, and identity of, expression control sequences will vary according to the type of cell in which the aggregation-disposed polypeptide sequence is to be expressed. Examples of expression control sequences include transcriptional promoters, enhancers, suitable mRNA ribosomal binding sites, and sequences that terminate transcription and translation.

Suitable expression control sequences can be selected by one of ordinary skill in the art. Standard methods can be used by the skilled person to construct expression vectors. See, generally, Sambrook et al., 1989, *Cloning—A Laboratory Manual* ($2^{nd}$ Ed), Cold Spring Harbor Laboratory Press, Cold Spring Harbor, N.Y.

Useful vectors include plasmid vectors and viral vectors. Viral vectors can be, for example, those derived from retroviruses, adenoviruses, adeno-associated virus, SV40 virus, pox viruses, or herpes viruses. Once introduced into a host cell (e.g., a bacterial cell, a yeast cell, an insect cell, an avian cell, or a mammalian cell), the vector can remain episomal, or be incorporated into the genome of the host cell. Useful vectors include vectors that can be purchased commercially, e.g., pcDNA 3.1-based vectors can be purchased from Invitrogen (Carlsbad, Calif.).

Compounds: Using assays such as those described above, we have identified certain compounds, which are categorized according to one of Formulas I-IV or one of Formulas V(a)-V(u). The invention encompasses these compounds in, for example, a substantially pure form, as well as various compositions containing one or more of them (e.g., pharmaceutical formulations, packaged products, and kits) and methods of using them.

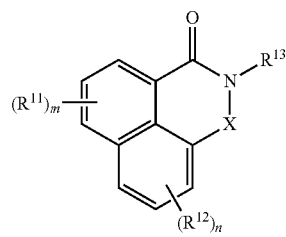

Formula I

Compounds that can be used in practicing the invention, having the general formula of Formula I can contain a benzo[de]isoquinoline-1,3-dione or 1H-benzo[cd]indol-2-one core. The core can be substituted, for example at the nitrogen, or on one or both of the phenyl moieties.

Any ring carbon atom can be substituted, for example with one or more $R^1$ and $R^2$ as defined above. For example, $R^1$ and $R^2$ can include, without limitation, halo, nitro, amino, hydroxy, alkoxy, alkyl, alkenyl, alkynyl, cyclyl, heterocyclyl, aryl, arylalkyl, heteroaryl, heteroarylalkyl, or amido, each of which can be further substituted with substituents. Examples of substituents include, but are not limited to halo, alkyl, alkoxy, or hydroxy.

The nitrogen is bound to $R^3$. Examples of $R^3$ include, but are not limited to H, alkyl, alkenyl, alkynyl, amino, hydroxy, aryl, arylalkyl, arylamino, heterocyclyl, heterocyclylalkyl, heteroaryl, heteroarylalkyl, cyclyl, cyclylalkyl, aminoalkyl, hydroxyalkyl, or alkoxyalkyl each of which can be further substituted with substituents. Examples of substituents include, but are not limited to halo, alkyl, amino, hydroxy, amido, or hydroxyalkyl.

In specific embodiments, the invention features a purified or substantially pure compound of Formula I and compositions comprising such compounds (e.g., pharmaceutical or physiologically acceptable compositions). Referring to Formula I, X can be C(O) or a bond; each $R^1$ and $R^2$ can be, independently halo, nitro, amino, hydroxy, alkoxy, alkyl, alkenyl, alkynyl, cyclyl, heterocyclyl, aryl, arylalkyl, heteroaryl, or heteroarylalkyl, $NR^5C(O)R^4$, or $C(O)NR^5R^6$; each of which can be optionally substituted with 1-4 $R^7$; $R^3$ can be H, alkyl, alkenyl, alkynyl, amino, hydroxy, aryl, arylalkyl, arylamino, heterocyclyl, heterocyclylalkyl, heteroaryl, heteroarylalkyl, cyclyl, cyclylalkyl, aminoalkyl, hydroxyalkyl, or alkoxyalkyl; each of which can be optionally substituted with 1-4 $R^8$; $R^4$ can be H, alkyl, alkenyl, alkynyl, cyclyl, heterocyclyl, aryl, or heteroaryl; each $R^5$ and $R^6$ can be, independently, H, hydroxy, alkoxy, alkyl, alkenyl, alkynyl, cyclyl, heterocyclyl, aryl, arylalkyl, heteroaryl, or heteroarylalkyl; each $R^7$ can be, independently, halo, alkyl, alkoxy, or hydroxy; each $R^8$ can be, independently, halo, alkyl, amino, hydroxy, $C(O)NR^5R^6$, $NR^5C(O)R^4$, or hydroxyalkyl; and m and n can each be, independently, an integer from 0 to 3. In specific embodiments, $R^1$ can be heterocylcyl (e.g., in this embodiment and others, $R^1$ can be a nitrogen-containing heterocyclyl), nitro or amino; m can be 1; and n can be 0. In other embodiments, $R^1$ can be morpholinyl, piperidinyl, or piperazinyl. Each $R^1$ and $R^2$ can be, independently halo, and each of m and n can be, independently, 1. Either or both of $R^1$ and $R^2$ can be chloro. Either or both of m and n can be 0.

$R^3$ can be H, alkyl, amino, aryl, arylamino, arylalkyl, heterocyclylalkyl (e.g., morpholinyl, piperidinyl or piperazinyl that includes a $C_2$-$C_4$ alkyl) aminoalkyl, hydroxyalkyl, or alkoxyalkyl. When $R^3$ is an aminoalkyl, it can be optionally substituted with alkyl, hydroxyalkyl or $C(O)NR^5R^6$.

In specific embodiments, X is C(O); $R^1$ is heterocylcyl (e.g., a nitrogen-containing heterocyclyl), nitro or amino; $R^3$ is alkyl, amino, aryl, arylamino, arylalkyl, heterocyclylalkyl, aminoalkyl, hydroxyalkyl, or alkoxyalkyl; m is 1; and n is 0. More specifically, $R^1$ can be morpholinyl, piperidinyl, or piperazinyl. Where $R^3$ is aminoalkyl, it can be optionally substituted with hydroxyalkyl or $C(O)NR^5R^6$.

In another embodiment, X is C(O); $R^1$ and $R^2$ are each independently halo; $R^3$ is alkyl, amino, aryl, arylamino, arylalkyl, heterocyclylalkyl, aminoalkyl, hydroxyalkyl, or alkoxyalkyl; and m and n are each independently 1. For example, $R^3$ can be heterocyclylalkyl or aminoalkyl, and where $R^3$ is aminoalkyl, it can be optionally substituted with hydroxyalkyl or $C(O)NR^5R^6$.

In another embodiment, X is C(O); $R^3$ is alkyl, amino, aryl, arylamino, arylalkyl, heterocyclylalkyl, aminoalkyl, hydroxyalkyl, or alkoxyalkyl; and m and n are each independently 0. For example, $R^3$ can be heterocyclylalkyl or aminoalkyl, and where $R^3$ is aminoalkyl, it can be optionally substituted with alkyl, hydroxyalkyl or $C(O)NR^5R^6$. In this or other embodiments, where an R group (e.g., $R^3$) is heterocyclylalkyl, the heterocyclylalkyl can include a heterocyclyl of morpholinyl, piperidinyl and piperazinyl, and the heterocyclylalkyl can include a $C_2$-$C_4$ alkyl.

In another embodiment, X is a bond, and $R^3$ is H or alkyl. $R^2$ can be amino, nitro, or $NR^5C(O)R^4$, and n can be 1. Alternatively, m and n can be 0.

The compounds and compositions of the invention can be, or can include: 2-Phenylamino-benzo[de]isoquinoline-1,3-dione; 2-Benzyl-6-morpholin-4-yl-benzo[de]isoquinoline-1,3-dione; 6-(4-Methyl-piperazin-1-yl)-2-phenyl-benzo[de]isoquinoline-1,3-dione; 2-(2-Morpholin-4-yl-ethyl)-benzo[de]isoquinoline-1,3-dione; 6-(1,3-Dioxo-1H,3H-benzo[de]isoquinolin-2-yl)-hexanoic acid hydroxyamide; 2-[3-(Hydroxymethyl-amino)-propyl]-benzo[de]isoquinoline-1,3-dione; 2-[2-(Hydroxymethyl-amino)-ethyl]-benzo[de]isoquinoline-1,3-dione; 2-(3-Methoxy-propyl)-benzo[de]isoquinoline-1,3-dione; 2-(3-Dimethylamino-propyl)-benzo[de]isoquinoline-1,3-dione; 2-(3-Morpholin-4-yl-propyl)-benzo[de]isoquinoline-1,3-dione; 2-(2-Piperidin-4-yl-ethyl)-benzo[de]isoquinoline-1,3-dione; 2-(3-Piperidin-1-yl-propyl)-benzo[de]isoquinoline-1,3-dione; 2-Dimethylamino-benzo[de]isoquinoline-1,3-dione; 2-(2-Dimethylamino-ethyl)-benzo[de]isoquinoline-1,3-dione; 2-(3-Methyl-butyl)-benzo[de]isoquinoline-1,3-dione; 6,7-Dichloro-2-(2-dimethylamino-ethyl)-benzo[de]isoquinoline-1,3-dione; 2-(2-Piperidin-1-yl-ethyl)-benzo[de]isoquinoline-1,3-dione; 2-(2-Piperazin-1-yl-ethyl)-benzo[de]isoquinoline-1,3-dione; 2-(2-Morpholin-4-yl-ethyl)-benzo[de]isoquinoline-1,3-dione; 2-(2-Diethylamino-ethyl)-benzo[de]isoquinoline-1,3-dione; 6-Amino-1H-benzo[cd]indol-2-one; 1-Ethyl-1H-benzo[cd]indol-2-one; 6-Amino-1-ethyl-1H-benzo[cd]indol-2-one; N-(1-Ethyl-2-oxo-1,2-dihydro-benzo[cd]indol-6-yl)-acetamide; N-Ethyl-2-(2-oxo-2H-benzo[cd]indol-1-yl)-acetamide; 2-Butyl-benzo[de]isoquinoline-1,3-dione; 2-(2-Methoxy-ethyl)-benzo[de]isoquinoline-1,3-dione; 2-Hydroxymethyl-6-piperidin-1-yl-benzo[de]isoquinoline-1,3-dione; 6-(4-Methyl-piperazin-1-yl)-2-phenyl-benzo[de]isoquinoline-1,3-dione; and/or 2-[3-(Hydroxymethyl-amino)-propyl]-benzo[de]isoquinoline-1,3-dione. For example, the compounds and compositions of the invention can be, or can include a compound shown in Table 1.

TABLE 1

| GI | | Formula I |
|---|---|---|
| | 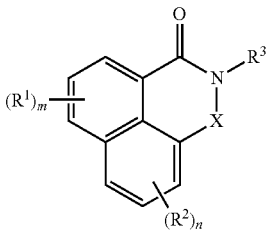 $(R^1)_m$ ... $(R^2)_n$ ... $R^3$, X | |
| A1 | 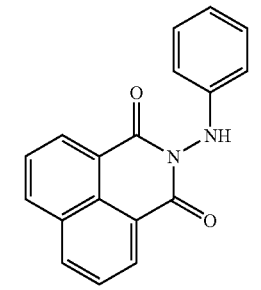 | 2-Phenylamino-benzo[de]isoquinoline-1,3-dione |
| A2 aka C7 aka C4 | 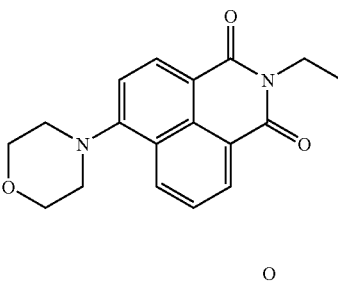 | 2-Benzyl-6-morpholin-4-yl-benzo[de]isoquinoline-1,3-dione |
| A3 aka C4-34 | | 6-(4-Methyl-piperazin-1-yl)-2-phenyl-benzo[de]isoquinoline-1,3-dione |

TABLE 1-continued

| GI | | Formula I |
|---|---|---|
| A4 | 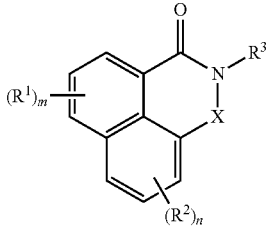 | 2-(2-Morpholin-4-yl-ethyl)-benzo[de]isoquinoline-1,3-dione |
| A5 Scriptaid | 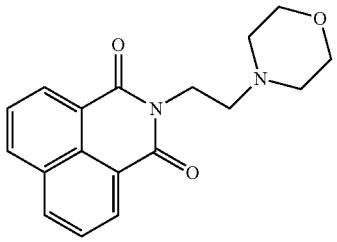 [SMILES: O=C1c2cccc3cccc(c23)C(=O)N1CCN1CCOCC1] | 6-(1,3-Dioxo-1H,3H-benzo[de]isoquinolin-2-yl)-hexanoic acid hydroxyamide |
| A6 | 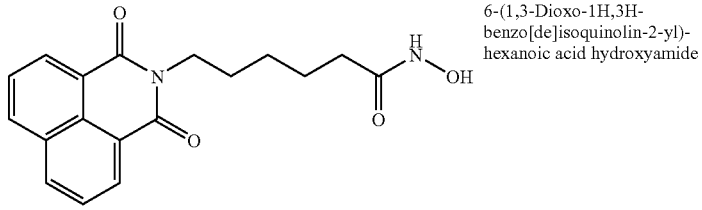 | 2-[3-(Hydroxymethyl-amino)-propyl]-benzo[de]isoquinoline-1,3-dione |
| A7 aka C9-3 | 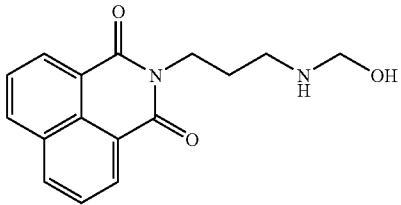 [SMILES: O=C1c2cccc3cccc(c23)C(=O)N1CCCNCO] | 2-[2-(Hydroxymethyl-amino)-ethyl]-benzo[de]isoquinoline-1,3-dione |
| A8 aka C9-2 | 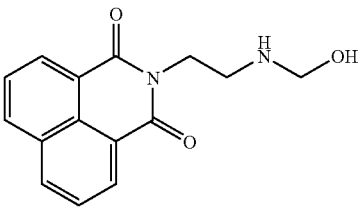 [SMILES: O=C1c2cccc3cccc(c23)C(=O)N1CCNCO] | 2-(3-Methoxy-propyl)-benzo[de]isoquinoline-1,3-dione |
| A9 aka C9-1 aka C91 | 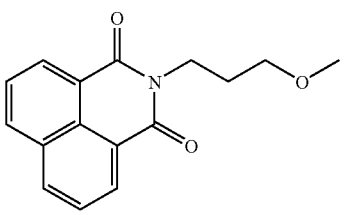 [SMILES: COCCCN1C(=O)c2cccc3cccc(c23)C1=O] | 2-(3-Dimethylamino-propyl)-benzo[de]isoquinoline-1,3-dione |

TABLE 1-continued
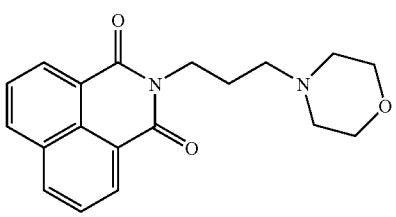 [SMILES: O=C1c2cccc3cccc(c23)C(=O)N1CCCN1CCOCC1]
| GI | | Formula I |
|---|---|---|
| A10 | 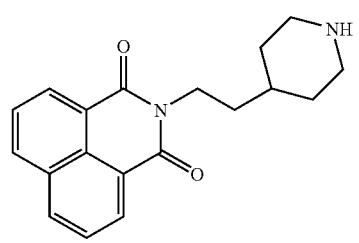 [SMILES: O=C1c2cccc3cccc(c23)C(=O)N1CCC1CCNCC1] | 2-(3-Morpholin-4-yl-propyl)-benzo[de]isoquinoline-1,3-dione |
| A11 aka C9-7 | 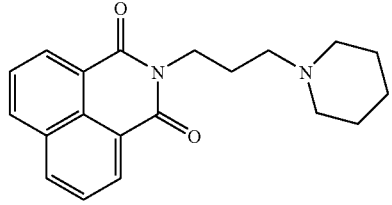 [SMILES: O=C1c2cccc3cccc(c23)C(=O)N1CCCN1CCCCC1] | 2-(2-Piperidin-4-yl-ethyl)-benzo[de]isoquinoline-1,3-dione |
| A12 aka C9-4A | 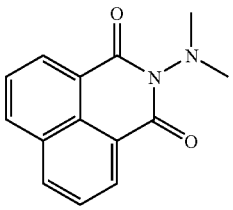 [SMILES: CN(C)N1C(=O)c2cccc3cccc(c23)C1=O] | 2-(3-Piperidin-1-yl-propyl)-benzo[de]isoquinoline-1,3-dione |
| A13 | 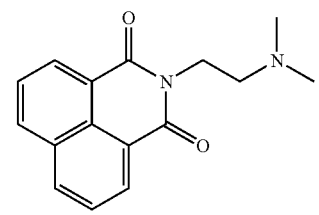 [SMILES: CN(C)CCN1C(=O)c2cccc3cccc(c23)C1=O] | 2-Dimethylamino-benzo[de]isoquinoline-1,3-dione |
| A14 aka C9-1B | 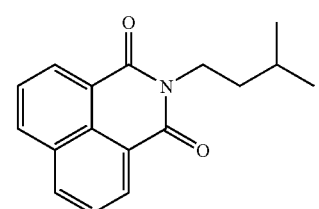 | 2-(2-Dimethylamino-ethyl)-benzo[de]isoquinoline-1,3-dione |
| A15 aka C9-1A | | 2-(3-Methyl-butyl)-benzo[de]isoquinoline-1,3-dione |

TABLE 1-continued
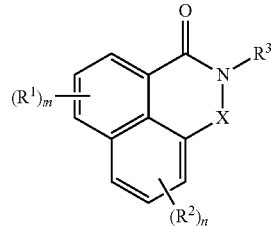
| GI | | Formula I |
|---|---|---|
| A16 aka C9-1 aka C1 | | 6,7-Dichloro-2-(2-dimethylamino-ethyl)-benzo[de]isoquinoline-1,3-dione |
| A17 | | 2-(2-Dimethylamino-ethyl)-5-nitro-benzo[de]isoquinoline-1,3-dione |
| A18 | | 5-Amino-2-(2-dimethylamino-ethyl)-benzo[de]isoquinoline-1,3-dione |
| A19 aka C9-4 | | 2-(2-Piperidin-1-yl-ethyl)-benzo[de]isoquinoline-1,3-dione |
| A20 aka C9-5 | | 2-(2-Piperazin-1-yl-ethyl)-benzo[de]isoquinoline-1,3-dione |

TABLE 1-continued
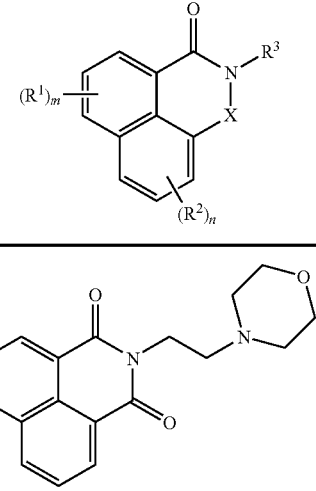
| GI | | Formula I |
|---|---|---|
| A21 | 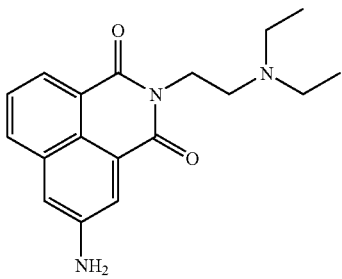 [SMILES: CCN(CC)CCN1C(=O)c2cccc3cc(N)cc(c23)C1=O] | 2-(2-Morpholin-4-yl-ethyl)-benzo[de]isoquinoline-1,3-dione |
| A22 aka C96C | 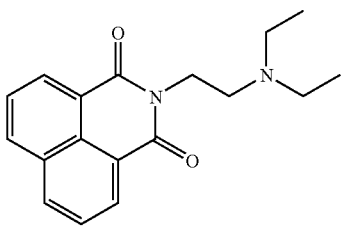 [SMILES: CCN(CC)CCN1C(=O)c2cccc3cccc(c23)C1=O] | 5-Amino-2-(2-diethylamino-ethyl)-benzo[de]isoquinoline-1,3-dione |
| A23 aka C9-6B | 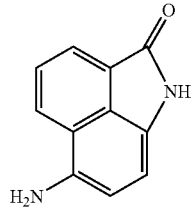 [SMILES: Nc1ccc2c3c(cccc13)C(=O)N2] | 2-(2-Diethylamino-ethyl)-benzo[de]isoquinoline-1,3-dione |
| A24 | 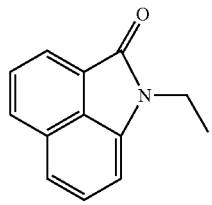 | 6-Amino-1H-benzo[cd]indol-2-one |
| A25 |  | 1-Ethyl-1H-benzo[cd]indol-2-one |

TABLE 1-continued

| GI | | Formula I |
|---|---|---|
| A26 | | 6-Amino-1-ethyl-1H-benzo[cd]indol-2-one |
| A27 aka CG4 | | N-(1-Ethyl-2-oxo-1,2-dihydro-benzo[cd]indol-6-yl)-acetamide |
| A28 | | N-Ethyl-2-(2-oxo-2H-benzo[cd]indol-1-yl)-acetamide |
| A29 | | 2-Butyl-benzo[de]isoquinoline-1,3-dione |
| A30 | | 2-(2-Methoxy-ethyl)-benzo[de]isoquinoline-1,3-dione |
| A31 aka C4-7 | | 2-Hydroxymethyl-6-piperidin-1-yl-benzo[de]isoquinoline-1,3-dione |

TABLE 1-continued

| | | |
|---|---|---|
| GI | (structure: Formula I with $(R^1)_m$, $(R^2)_n$, $R^3$, X) | Formula I |
| A33 aka C9 aka C4-DAK | (structure) | 2-[3-(Hydroxymethyl-amino)-propyl]-benzo[de]isoquinoline-1,3-dione |
| A34 | (structure) | |
| A35 | (structure) | N-(1-ethyl-2-oxo-1,2-dihydrobenzo[cd]indol-7-yl)acetamide |

While pharmaceutical formulations are described further below, we note here, that the compounds of the invention, including those just described, can be formulated for oral or parenteral administration to a patient. Likewise, while methods are described further elsewhere herein, we note that the invention encompasses methods of treating a subject who has, who has been diagnosed as having, or who is at risk of developing, a disorder characterized by an undesirable association of proteins. The methods can include the step of identifying the subject (or patient) and administering to the subject a therapeutically effective amount of a pharmaceutical composition that includes any of the compounds described herein (e.g., a compound conforming to Formula I). The subject may have been diagnosed as having, or at risk of developing, Huntington's disease, Parkinson's disease, spinal and bulbar muscular atrophy, dentatorubral-pallidoluysian atrophy, spinocerebellar ataxia type 1 (SCA1), SCA2, SCA6, SCA7, Machado-Joseph disease (MJD/SCA3), a carcinoma associated with oncoprotein association (e.g., dimerization) (e.g., breast cancer), amyloidosis, myeloma, Creutzfeldt-Jakob disease, kuru, cystic fibrosis, neuroblastoma, or alpha-1-antitrypsin deficiency disease.

With respect to C9, which conforms to Formula I, our initial studies revealed that this compound increases protein-protein aggregation (as described further below, C9 facilitated aggregation of polyglutamine-containing proteins in a cell-free membrane-trapping assay and in neurons in cultured brain slices at concentrations higher than 10 μM). Based on this information, we readily identified two compounds that are variants of C9 that also facilitate protein-protein aggregation (C9-1 and C9-2, shown below). Accordingly, C9, C9-1 and C9-2 are within the scope of the present invention and can be formulated in pharmaceutically or physiologically acceptable compositions and applied to cells to, we believe, facilitate association between polypeptides. Our present results lead us to conclude that C9 interferes with transcriptional machinery, possibly by intercalating into the DNA's double helix and forming high affinity hydrogen bonds with GC rich motifs.

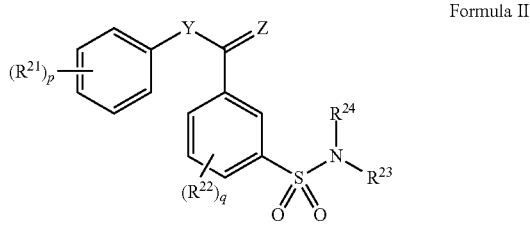

Formula II

In Formula II, Z can be O or S; Y can be O, $NR^{25}$ or $CR^{26}R^{27}$; each of $R^{21}$ and $R^{22}$ can be independently halo (e.g., bromo), hydroxy, nitro, cyano, amino, amido, or alkyl; $R^{23}$ can be alkyl, cyclyl, aryl, heteroaryl, cyclylalkyl, arylalkyl, or heteroarylalkyl, or can be taken together with $R^{24}$ and the nitrogen to which it is attached to form a ring where $R^{23}$ is optionally substituted with 1-3 $R^{28}$. $R^{24}$ can be H or alkyl, or can be taken together with $R^{23}$ and the nitrogen to which it is attached to form a ring where $R^{24}$ is optionally substituted with 1-3 $R^{28}$; $R^{25}$ can be H or alkyl; each of $R^{26}$ and $R^{27}$ can be, independently, H or alkyl; each $R^{28}$ can be independently halo (e.g., bromo), hydroxy, nitro, cyano, amino, amido, or alkyl; and each p and q can be, independently, an integer from 0-4. Specific compounds that conform to Formula II are shown in Table 2.

In specific embodiments, the invention features a purified or substantially pure compound of Formula II and compositions comprising such compounds (e.g., pharmaceutical or physiologically acceptable compositions). Referring to Formula II, Z can be O or S; Y can O, $NR^{25}$ or $CR^{26}R^{27}$; each of $R^{21}$ and $R^{22}$ can be, independently, halo, hydroxy, nitro, cyano, amino, amido, or alkyl; $R^{23}$ can be alkyl, cyclyl, aryl, heteroaryl, cyclylalkyl, arylalkyl, or heteroarylalkyl, or when taken together with $R^{24}$ and the nitrogen to which it is attached can form a ring. For example, $R^{23}$ can optionally be substituted with 1-3 $R^{28}$. $R^{24}$ can be H, alkyl, or when taken together with $R^{23}$ and the nitrogen to which it is attached can form a ring. For example, $R^{24}$ can be optionally substituted with 1-3 $R^{28}$. $R^{25}$ can be H or alkyl; each of $R^{26}$ and $R^{27}$ can be, independently, H or alkyl; each $R^{28}$ can be, independently, halo, hydroxy, nitro, cyano, amino, amido, or alkyl; each p can be an integer from 0-5, inclusive; and each q can be, independent of p, an integer from 0-4, inclusive (i.e., 0, 1, 2, 3, or 4).

In specific embodiments, Z is O, and Y is $NR^{25}$. In this embodiment and others, $R^{25}$ can be H. Alternatively, Y can be $CR^{26}R^{27}$. Each $R^{21}$ and $R^{22}$ can be independently halo or hydroxy. In some embodiments, $R^{21}$ is halo and p is 1. In that instance, q can be, for example, 0. In connection with Formula II or any other of the formulas presented herein, the halogen can be any radical of fluorine, chlorine, bromine or iodine. Thus, in specific embodiments, $R^{22}$ can be halo (e.g., bromo) and q can be 1. In that instance, p can be, for example, 0. In some embodiments, p and q are 0.

$R^{23}$ can be cyclyl or aryl, and the aryl can be substituted with bromo. $R^{24}$ can be H or alkyl, and $R^{23}$ and $R^{24}$, taken together with the nitrogen to which they are attached, can form a ring.

In another embodiment, Z is O; Y is $NR^{25}$; each of $R^{21}$ and $R^{22}$ are, independently, halo (e.g., bromo), hydroxy or alkyl; $R^{23}$ is cyclyl or aryl; $R^{24}$ is H or alkyl; and each p and q is 0 or 1.

In another embodiment, Z is O; Y is $CR^{26}R^{27}$; each $R^{21}$ and $R^{22}$ is independently halo (e.g., bromo, chloro, fluoro, or iodo), hydroxy, or alkyl; $R^{23}$ and $R^{24}$, taken together with the nitrogen to which they are attached, can form a ring; and each p and q is 0 or 1. For example, $R^{21}$ can be hydroxy, p can be 1, and q can be 0.

The compounds and compositions of the invention can be, or can include: 4-Bromo-N-(4-bromo-phenyl)-3-cyclohexylsulfamoyl-benzamide; N-(4-Bromo-phenyl)-3-(4-bromo-phenylsulfamoyl)-benzamide; 3-(4-Bromo-phenylsulfamoyl)-N-phenyl-benzamide; 4-Bromo-3-cyclohexylsulfamoyl-N-phenyl-benzamide; N-(4-Bromo-phenyl)-3-cyclohexylsulfamoyl-benzamide; and/or 1-[3-(Azepane-1-sulfonyl)-2-bromo-phenyl]-2-(3-hydroxy-phenyl)-ethanone. For example, the compounds and compositions of the invention can be, or can include a compound shown in Table 2.

TABLE 2

| | | |
|---|---|---|
| GII | [structure of Formula II with $(R^{21})_p$, $(R^{22})_q$, Y, Z, $R^{23}$, $R^{24}$] | Formula II |
| B1 | [structure of 4-Bromo-N-(4-bromo-phenyl)-3-cyclohexylsulfamoyl-benzamide] | 4-Bromo-N-(4-bromo-phenyl)-3-cyclohexylsulfamoyl-benzamide |

TABLE 2-continued

| | Structure | Name |
|---|---|---|
| GII | Formula II (generic structure with $(R^{21})_p$-phenyl-Y-C(=Z)- group connected to benzene ring bearing $(R^{22})_q$ and $-SO_2-NR^{23}R^{24}$) | Formula II |
| B2 aka C2-8 aka C8 | N-(4-bromophenyl)benzamide with 3-sulfonamide to 4-bromophenyl | N-(4-Bromo-phenyl)-3-(4-bromo-phenylsulfamoyl)-benzamide |
| B3 | N-phenylbenzamide with 3-sulfonamide to 4-bromophenyl | 3-(4-Bromo-phenylsulfamoyl)-N-phenyl-benzamide |
| B4 | N-phenylbenzamide with 4-bromo and 3-cyclohexylsulfamoyl | 4-Bromo-3-cyclohexylsulfamoyl-N-phenyl-benzamide |
| B5 | N-(4-bromophenyl)benzamide with 3-cyclohexylsulfamoyl | N-(4-Bromo-phenyl)-3-cyclohexylsulfamoyl-benzamide |

TABLE 2-continued
| GII | | Formula II |
|---|---|---|
| | 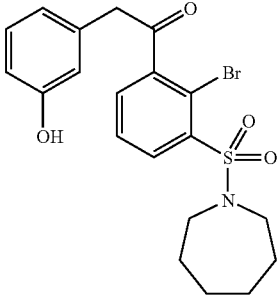 [SMILES: O=C(Cc1cccc(O)c1)c1cccc(S(=O)(=O)N2CCCCCC2)c1Br] | |
| B6 aka C2-10 | 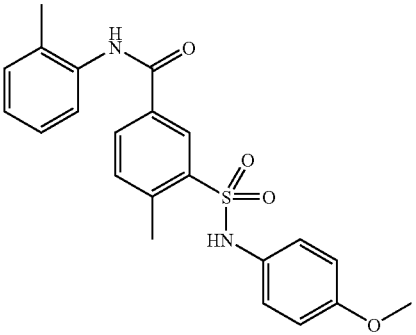 [SMILES: COc1ccc(NS(=O)(=O)c2cc(C(=O)Nc3ccccc3C)ccc2C)cc1] | 1-[3-(Azepane-1-sulfonyl)-2-bromo-phenyl]-2-(3-hydroxy-phenyl)-ethanone |
| B7 ala C2-11 | 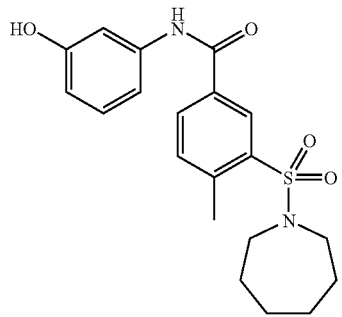 [SMILES: Cc1ccc(C(=O)Nc2cccc(O)c2)cc1S(=O)(=O)N1CCCCCC1] | 3-(N-4-methoxyphenyl)sulfamoyl)-4-methyl-N-o-tolylbenzamide |
| B8 | 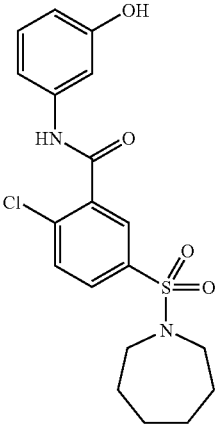 [SMILES: O=C(Nc1cccc(O)c1)c1cc(S(=O)(=O)N2CCCCCC2)ccc1Cl] | 3-(azepan-1-ylsulfonyl)-N-(3-hydroxyphenyl)-4-methylbenzamide |
| B9 | | 5-(azepan-1-ylsulfonyl)-2-chloro-N-(3-hydroxyphenyl)benzamide |

While pharmaceutical formulations are described further below, we note here, that the compounds of the invention, including those just described, can be formulated for oral or parenteral administration to a patient. Likewise, while methods are described further elsewhere herein, we note that the invention encompasses methods of treating a subject who has, who has been diagnosed as having, or who is at risk of developing, a disorder characterized by an undesirable association of proteins. The methods can include the step of identifying the subject (or patient) and administering to the subject a therapeutically effective amount of a pharmaceutical composition that includes any of the compounds described herein (e.g., a compound conforming to Formula II). The subject may have been diagnosed as having, or at risk of developing, Huntington's disease, Parkinson's disease, spinal and bulbar muscular atrophy, dentatorubral-pallidoluysian atrophy, spinocerebellar ataxia type 1 (SCA1), SCA2, SCA6, SCA7, Machado-Joseph disease (MJD/SCA3), a carcinoma associated with oncoprotein association (e.g., dimerization) (e.g., breast cancer), amyloidosis, myeloma, Creutzfeldt-Jakob disease, kuru, cystic fibrosis, neuroblastoma, or alpha-1-antitrypsin deficiency disease.

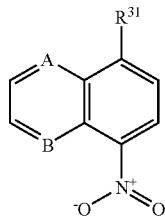

Formula III

In Formula III, A can be N or $CR^{32}$; B can be N or CH; $R^{31}$ can be H or $NR^{33}R^{34}$; $R^{31}$ can be optionally substituted with 1-3 $R^{35}$; $R^{32}$ can be H or $NR^{33}R^{34}$; $R^{32}$ can be optionally substituted with 1-3 $R^{35}$; $R^{33}$ can be H, alkyl, or taken together with $R^{34}$ and the nitrogen to which it is attached forms a heterocyclyl ring; $R^{34}$ can be H, alkyl, arylalkyl, heteroarylalkyl, cyclylalkyl, heterocyclylalkyl or taken together with $R^{33}$ and the nitrogen to which it is attached to form a heterocyclyl ring; each $R^{35}$ can be, independently, halo (e.g., bromo), hydroxy, amino, nitro, alkyl, aryl, arylacyl, arylalkyl, heteroaryl, heteroarylacyl, heteroarylalkyl; cyclylacyl; heterocyclylacyl; or alkylacyl; $R^{35}$ can be optionally substituted with 1-4 $R^{36}$; each $R^{36}$ can be, independently, halo (e.g., bromo), alkyl, nitro, amino or hydroxy. Specific compounds that conform to Formula III are shown in Table 3.

In specific embodiments, the invention features a purified or substantially pure compound of Formula III and compositions comprising such compounds (e.g., pharmaceutical or physiologically acceptable compositions). Referring to Formula III, A can be N or $CR^{32}$; B can be N or CH; $R^{31}$ can be H or $NR^{33}R^{34}$; wherein $R^{31}$ is optionally substituted with 1-3 $R^{35}$; $R^{32}$ can be H or $NR^{33}R^{34}$; wherein $R^{32}$ optionally substituted with 1-3 $R^{35}$; $R^{33}$ can be H, alkyl, or taken together with $R^{34}$ and the nitrogen to which it is attached, can form a heterocyclyl ring; $R^{34}$ can be H, alkyl, arylalkyl, heteroarylalkyl, cyclylalkyl, heterocyclylalkyl or, taken together with $R^{33}$ and the nitrogen to which it is attached, can form a heterocyclyl ring; each $R^{35}$ can be, independently halo, hydroxy, amino, nitro, alkyl, aryl, arylacyl, arylalkyl, heteroaryl, heteroarylacyl, heteroarylalkyl, cyclylacyl, heterocyclylacyl, or alkylacyl, wherein $R^{35}$ can be, optionally, substituted with 1-4 $R^{36}$; and each $R^{36}$ can be, independently, halo, alkyl, nitro, amino or hydroxy.

For example, A can be $CR^{32}$; B can be N; and $R^{32}$ can be H. $R^{31}$ can be $NR^{33}R^{34}$ and $R^{33}$ and $R^{34}$, together with the nitrogen to which they are attached, can form a heterocyclyl ring. For example, $R^{33}$ and $R^{34}$, together with the nitrogen to which they are attached, can form a ring (e.g., a piperazinyl, piperidinyl, or morpholinyl ring). The heterocyclyl ring can be substituted with $R^{35}$, which can be an alkyl, hydroxyl, or arylacyl group. Where $R^{35}$ is arylacyl, it can be substituted with 1-3 halo.

In another embodiment, A is N, B is CH, and $R^{31}$ is $NR^{33}R^{34}$. In this embodiment and others, $R^{33}$ and $R^{34}$, together with the nitrogen to which they are attached, can form a heterocyclyl ring (e.g., a piperazinyl, piperidinyl, or morpholinyl ring). The heterocyclyl ring can be substituted with $R^{35}$, which can be an alkyl, hydroxyl, or arylacyl. The araylacyl can be substituted with 1-3 halo.

In another embodiment, A is $CR^{32}$, B is N, $R^{31}$ is H, and $R^{32}$ is $NR^{33}R^{34}$. In this embodiment and others, $R^{33}$ and $R^{34}$, together with the nitrogen to which they are attached, can form a heterocyclyl ring (e.g., a piperazinyl or piperidinyl ring). The heterocyclyl ring can be substituted with $R^{35}$, which can be, for example, alkyl or arylacyl.

Accordingly, the compounds and compositions of the invention can be, or can include: (4-Chloro-phenyl)-[4-(8-nitro-quinolin-5-yl)-piperazin-1-yl]-methanone; (2-Chloro-4,5-difluoro-phenyl)-[4-(5-nitro-quinolin-8-yl)-piperazin-1-yl]-methanone; (2-Chloro-4,5-difluoro-phenyl)-[4-(8-nitro-quinolin-5-yl)-piperazin-1-yl]-methanone; (2-Fluoro-phenyl)-[4-(8-nitro-quinolin-5-yl)-piperazin-1-yl]-methanone; (3,4-Dichloro-phenyl)-[4-(5-nitro-quinolin-8-yl)-piperazin-1-yl]-methanone; 1-(8-Nitro-quinolin-5-yl)-piperidin-3-ol; (2-Fluoro-phenyl)-[4-(5-nitro-quinolin-8-yl)-piperazin-1-yl]-methanone; 8-Nitro-4-piperidin-1-yl-quinoline; 4-(4-Methyl-piperazin-1-yl)-8-nitro-quinoline; 5-Morpholin-4-yl-8-nitro-quinoline; (3-Morpholin-4-yl-propyl)-(8-nitro-quinolin-5-yl)-amine; 8-Nitro-5-piperazin-1-yl-quinoline; 8-(4-Methyl-piperazin-1-yl)-5-nitro-quinoline; and/or 5-Nitro-8-(4-phenyl-piperazin-1-yl)-quinoline. For example, the compounds and compositions of the invention can be, or can include a compound shown in Table 3.

TABLE 3
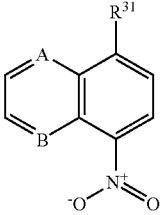
| GIII | | Formula III |
| E1 | 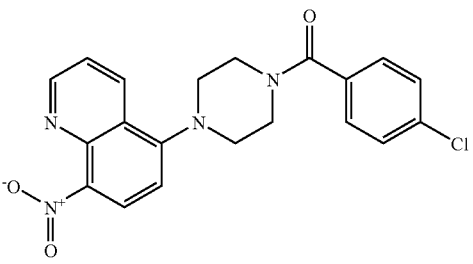 | (4-Chloro-phenyl)-[4-(8-nitro-quinolin-5-yl)-piperazin-1-yl]-methanone |
| E2 | 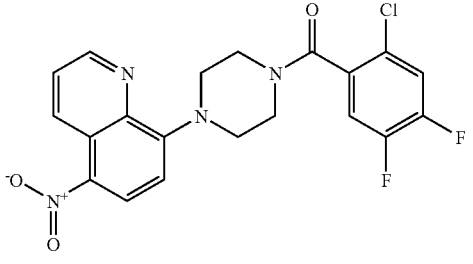 | (2-Chloro-4,5-difluoro-phenyl)-[4-(5-nitro-quinolin-8-yl)-piperazin-1-yl]-methanone |
| E3 | 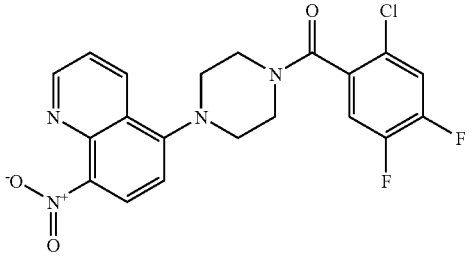 | (2-Chloro-4,5-difluoro-phenyl)-[4-(8-nitro-quinolin-5-yl)-piperazin-1-yl]-methanone |
| E4 | 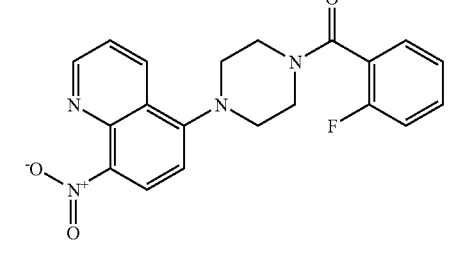 | (2-Fluoro-phenyl)-[4-(8-nitro-quinolin-5-yl)-piperazin-1-yl]-methanone |
| E5 | 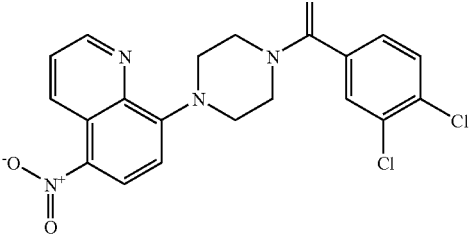 | (3,4-Dichloro-phenyl)-[4-(5-nitro-quinolin-8-yl)-piperazin-1-yl]-methanone |

TABLE 3-continued
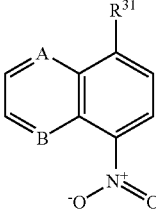
| GIII | | Formula III |
|---|---|---|
| E7 | 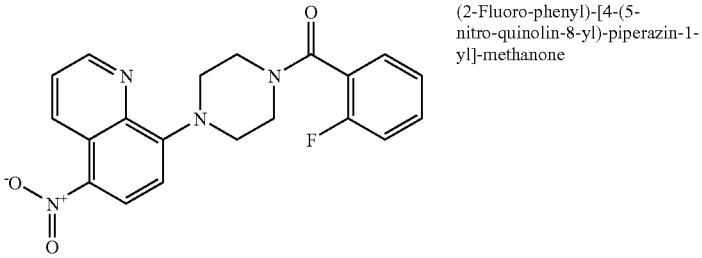 | (2-Fluoro-phenyl)-[4-(5-nitro-quinolin-8-yl)-piperazin-1-yl]-methanone |
| E8 | 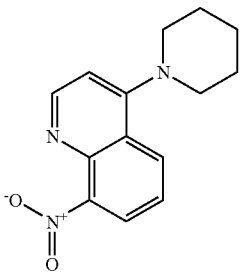 | 8-Nitro-4-piperidin-1-yl-quinoline |
| E9 | 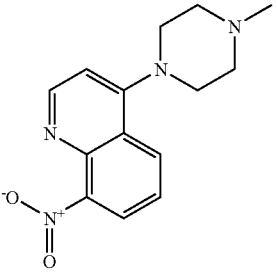 | 4-(4-Methyl-piperazin-1-yl)-8-nitro-quinoline |
| E10 | 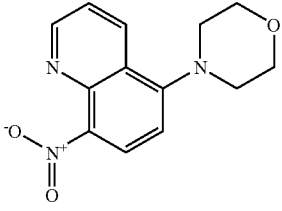 | 5-Morpholin-4-yl-8-nitro-quinoline |
| E11 | 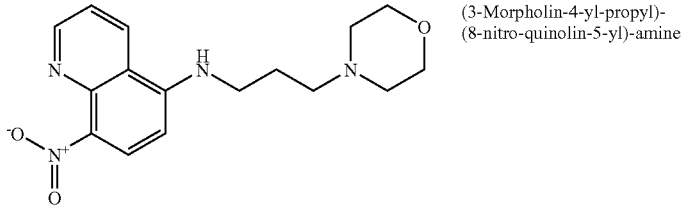 | (3-Morpholin-4-yl-propyl)-(8-nitro-quinolin-5-yl)-amine |

TABLE 3-continued

| | | |
|---|---|---|
| GIII | 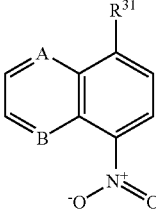 | Formula III |
| E12 | 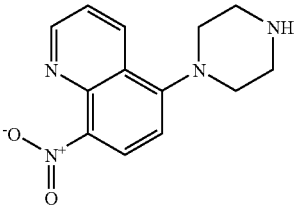 | 8-Nitro-5-piperazin-1-yl-quinoline |
| E13 | 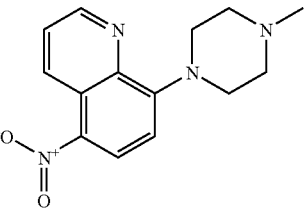 | 8-(4-Methyl-piperazin-1-yl)-5-nitro-quinoline |
| E14 | 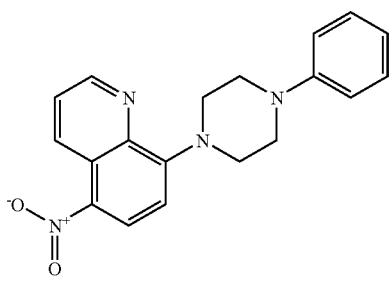 | 5-Nitro-8-(4-phenyl-piperazin-1-yl)-quinoline |

While pharmaceutical formulations are described further below, we note here, that the compounds of the invention, including those just described, can be formulated for oral or parenteral administration to a patient. Likewise, while methods are described further elsewhere herein, we note that the invention encompasses methods of treating a subject who has, who has been diagnosed as having, or who is at risk of developing, a disorder characterized by an undesirable association of proteins. The methods can include the step of identifying the subject (or patient) and administering to the subject a therapeutically effective amount of a pharmaceutical composition that includes any of the compounds described herein (e.g., a compound conforming to Formula III). The subject may have been diagnosed as having, or at risk of developing, Huntington's disease, Parkinson's disease, spinal and bulbar muscular atrophy, dentatorubral-pallidoluysian atrophy, spinocerebellar ataxia type 1 (SCA1), SCA2, SCA6, SCA7, Machado-Joseph disease (MJD/SCA3), a carcinoma associated with oncoprotein association (e.g., dimerization) (e.g., breast cancer), amyloidosis, myeloma, Creutzfeldt-Jakob disease, kuru, cystic fibrosis, neuroblastoma, or alpha-1-antitrypsin deficiency disease.

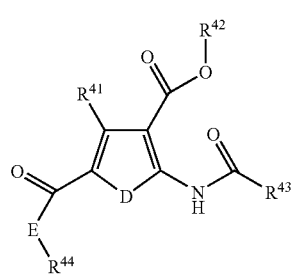

Formula IV

In Formula IV, D can be O, S, or NH; E can be O or NH; $R^{41}$ can be halo (e.g., bromo), alkyl, amino, hydroxy, alkoxy; $R^{42}$ can be alkyl, arylalkyl, cyclyl, or cyclylalkyl; $R^{43}$ can be alkyl, alkenyl, alkynyl, aryl, arylalkyl, heteroaryl, heteroarylalkyl, cyclyl, cyclylalkyl, heterocyclyl, or heterocyclylalkyl, where $R^{43}$ is optionally substituted with 1-4 $R^{45}$; $R^{44}$ can be alkyl, cyclyl, cyclylalkyl, aryl, arylalkyl, heteroaryl, heteroarylalkyl, heterocyclyl, or heterocyclylalkyl, where $R^{44}$ is optionally substituted with 1-4 $R^{46}$; each $R^{45}$ can be independently halo (e.g., bromo), alkyl, amino, amido, hydroxy, alkoxy, nitro, cyano, thio, alkylthio, sulfonyl, or sulfonamidyl; and each $R^{46}$ can be independently halo (e.g., bromo), alkyl, amino, amido, hydroxy, alkoxy, nitro, cyano, thio, alkylthio, sulfonyl, or sulfonamidyl. Specific compounds that conform to Formula IV are shown in Table 4.

In specific embodiments, the invention features a purified or substantially pure compound of Formula IV and compositions comprising such compounds (e.g., pharmaceutical or physiologically acceptable compositions). Referring to Formula IV, D can be O, S, or NH; E can be O or NH; $R^{41}$ can be halo, alkyl, amino, hydroxy, alkoxy; $R^{42}$ can be alkyl, arylalkyl, cyclyl, or cyclylalkyl; $R^{43}$ can be alkyl, alkenyl, alkynyl, aryl, arylalkyl, heteroaryl, heteroarylalkyl, cyclyl, cyclylalkyl, heterocyclyl, heterocyclylalkyl, wherein $R^{43}$ is optionally substituted with 1-4 $R^{45}$; $R^{44}$ can be alkyl, cyclyl, cyclylalkyl, aryl, arylalkyl, heteroaryl, heteroarylalkyl, heterocyclyl, or heterocyclylalkyl, wherein $R^{44}$ is optionally substituted with 1-4 $R^{46}$; each $R^{45}$ can be, independently, halo (e.g., bromo), alkyl, amino, amido, hydroxy, alkoxy, nitro, cyano, thio, alkylthio, sulfonyl, or sulfonamidyl; and each $R^{46}$ can be, independently, halo, alkyl, amino, amido, hydroxy, alkoxy, nitro, cyano, thio, alkylthio, sulfonyl, or sulfonamidyl. For example, D can be S, $R^{41}$ can be alkyl or methyl, E can be NH, $R^{44}$ can be alkyl or aryl (e.g., aryl substituted with alkoxy).

In other embodiments, E can be O, and $R^{42}$ and $R^{44}$ can be alkyl (e.g., $C_{2-3}$ alkyl). In this or other embodiments, $R^{42}$ can be ethyl or isopropyl. In this or other embodiments, $R^{43}$ can be aryl or arylalkyl (e.g., $R^{43}$ can be aryl substituted with 1-4 halo, alkyl, or sulfonamidyl groups or arylalkyl substituted with alkoxy).

In some embodiments, D can be S; E can be NH; $R^{41}$ can be alkyl; and $R^{42}$ can be alkyl. In this or other embodiments, $R^{43}$ can be aryl or arylalkyl (e.g., $R^{43}$ can be aryl substituted with 1-4 halo, alkyl, or sulfonamidyl groups or arylalkyl substituted with alkoxy). $R^{44}$ can be alkyl or aryl (e.g., aryl substituted with alkoxy).

In another embodiment, D can be S; E can be O; $R^{41}$ can be alkyl; and $R^{42}$ can be alkyl. Further, $R^{43}$ can be aryl, and $R^{44}$ can be alkyl. $R^{43}$ can aryl substituted with two chloro and one sulfonamidyl.

Accordingly, the compounds and compositions of the invention can be, or can include: 2-[2-(4-Methoxy-phenyl)-acetylamino]-5-(2-methoxy-phenylcarbamoyl)-4-methyl-thiophene-3-carboxylic acid ethyl ester; 5-(2-Methoxy-phenylcarbamoyl)-4-methyl-2-(2-methyl-benzoylamino)-thiophene-3-carboxylic acid ethyl ester; 5-Diethylcarbamoyl-2-(4-fluoro-benzoylamino)-4-methyl-thiophene-3-carboxylic acid isopropyl ester; or 5-(2,4-Dichloro-5-sulfamoyl-benzoylamino)-3-methyl-thiophene-2,4-dicarboxylic acid diethyl ester. The invention encompasses the compounds shown in Table 4 and compositions containing them.

TABLE 4

| GIV | | Formula IV |
|---|---|---|
| | Formula IV structure with $R^{41}$, $R^{42}$, $R^{43}$, $R^{44}$, D, E | |
| D1 | Structure | 2-[2-(4-Methoxy-phenyl)-acetylamino]-5-(2-methoxy-phenylcarbamoyl)-4-methyl-thiophene-3-carboxylic acid ethyl ester |
| D2 | Structure | 5-(2-Methoxy-phenylcarbamoyl)-4-methyl-2-(2-methyl-benzoylamino)-thiophene-3-carboxylic acid ethyl ester |

TABLE 4-continued

| | | |
|---|---|---|
| GIV | 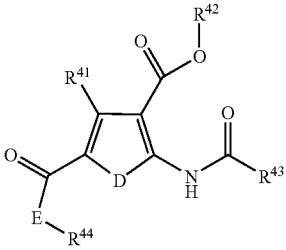 | Formula IV |
| D3 |  | 5-Diethylcarbamoyl-2-(4-fluoro-benzoylamino)-4-methyl-thiophene-3-carboxylic acid isopropyl ester |
| D4 | 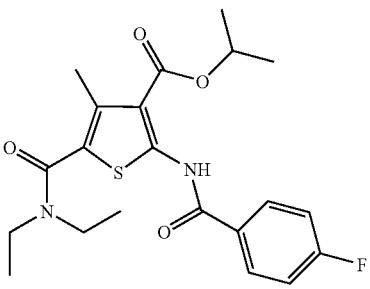 [SMILES: CCN(CC)C(=O)c1sc(NC(=O)c2ccc(F)cc2)c(C(=O)OC(C)C)c1C] | 5-(2,4-Dichloro-5-sulfamoyl-benzoylamino)-3-methyl-thiophene-2,4-dicarboxylic acid diethyl ester |

Further with respect to Formula IV, and in some embodiments, $R^{41}$ is alkyl, for example a lower alkyl, such as methyl, ethyl, propyl, or butyl. Preferred embodiments may include those where $R^{41}$ is methyl.

The core can also be substituted with an ester, for example, as depicted above as $C(O)OR^{42}$. Examples of suitable $R^{42}$ moieties include, but are not limited to alkyl, arylalkyl, cyclyl, or cyclylalkyl. The core can also be substituted with at least one amide positioned adjacent to the heteroatom. For example, as can be seen above, the core is substituted with $NHC(O)R^{43}$. Examples of $R^{43}$ include, but are not limited to alkyl, alkenyl, alkynyl, aryl, arylalkyl, heteroaryl, heteroarylalkyl, cyclyl, cyclylalkyl, heterocyclyl, heterocyclylalkyl. In some instances, $R^{43}$ is further substituted with one or more substituents, including for example, halo, alkyl, amino, amido, hydroxy, alkoxy, nitro, cyano, thio, alkylthio, sulfonyl, or sulfonamidyl.

The core can be substituted with an additional carbonyl, for example an ester or an amide. In preferred embodiment, the core is substituted as above with $C(O)NHR^{44}$. Examples of $R^{44}$ include, but are not limited to alkyl, cyclyl, cyclylalkyl, aryl, arylalkyl, heteroaryl, heteroarylalkyl, heterocyclyl, or heterocyclylalkyl. In some instances, $R^{44}$ is further substituted with one or more substituents, including for example, halo, alkyl, amino, amido, hydroxy, alkoxy, nitro, cyano, thio, alkylthio, sulfonyl, or sulfonamidyl.

While pharmaceutical formulations are described further below, we note here, that the compounds of the invention, including those just described, can be formulated for oral or parenteral administration to a patient. Likewise, while methods are described further elsewhere herein, we note that the invention encompasses methods of treating a subject who has, who has been diagnosed as having, or who is at risk of developing, a disorder characterized by an undesirable association of proteins. The methods can include the step of identifying the subject (or patient) and administering to the subject a therapeutically effective amount of a pharmaceutical composition that includes any of the compounds described herein (e.g., a compound conforming to Formula IV). The subject may have been diagnosed as having, or at risk of developing, Huntington's disease, Parkinson's disease, spinal and bulbar muscular atrophy, dentatorubral-pallidoluysian atrophy, spinocerebellar ataxia type 1 (SCA1), SCA2, SCA6, SCA7, Machado-Joseph disease (MJD/SCA3), a carcinoma associated with oncoprotein association (e.g., dimerization) (e.g., breast cancer), amyloidosis, myeloma, Creutzfeldt-Jakob disease, kuru, cystic fibrosis, neuroblastoma, or alpha-1-antitrypsin deficiency disease.

The compounds of Formulas V(a) through V(u) are shown in Table 5.

TABLE 5

Compound M1
Formula V(a)

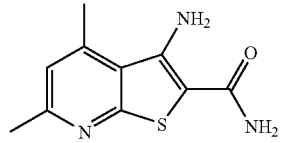

3-Amino-4,6-dimethyl-thieno[2,3-b]pyridine-2-carboxylic acid amide

Compound M2
Formula V(b)

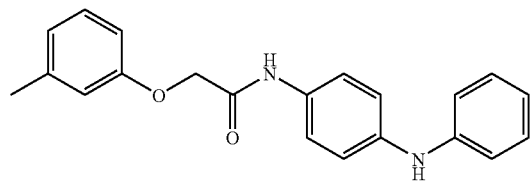 [SMILES: Cc1cccc(OCC(=O)Nc2ccc(Nc3ccccc3)cc2)c1]

N-(4-Phenylamino-phenyl)-2-m-tolyloxy-acetamide

Compound M3
Formula V(c)

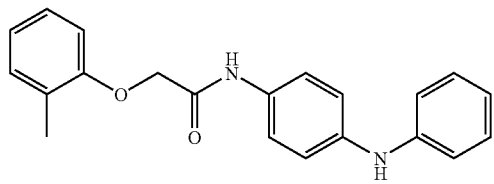 [SMILES: Cc1ccccc1OCC(=O)Nc1ccc(Nc2ccccc2)cc1]

N-(4-(phenylamino)phenyl)-2-(o-tolyloxy)acetamide

Compound M4
Formula V(d)

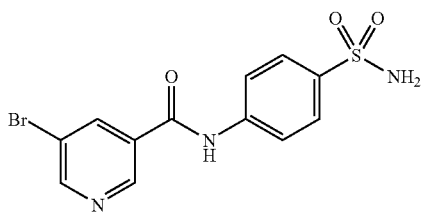 [SMILES: NS(=O)(=O)c1ccc(NC(=O)c2cncc(Br)c2)cc1]

5-Bromo-N-(4-sulfamoyl-phenyl)-nicotinamide

Compound M5
Formula V(e)

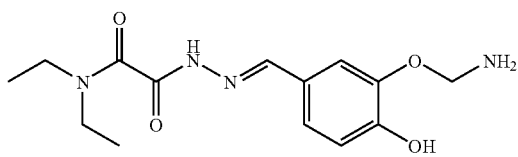 [SMILES: CCN(CC)C(=O)C(=O)N/N=C/c1ccc(O)c(OCN)c1]

2-[N'-(3-Aminomethoxy-4-hydroxy-benzylidene)-hydrazino]-N,N-diethyl-2-oxo-acetamide Compound M6
Formula V(f)

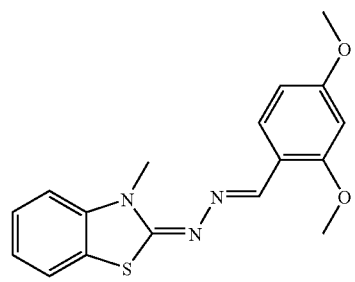 [SMILES: COc1ccc(/C=N/N=c2/sc3ccccc3n2C)c(OC)c1]

N-(2,4-Dimethoxy-benzylidene)-N-(3-methyl-3H-benzothiazol-2-ylidene)-hydrazine

TABLE 5-continued

Compound M7
Formula V(g)

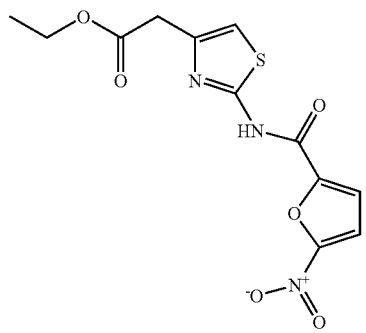

{2-[(5-Nitro-furan-2-carbonyl)-amino]-thiazol-4-yl}-
acetic acid ethyl ester

Compound M8
Formula V(h)

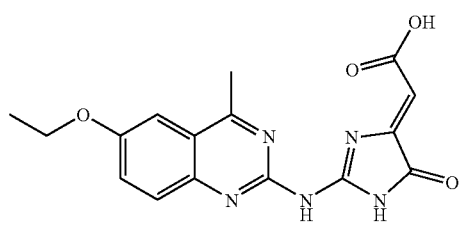 [SMILES: CCOc1ccc2nc(NC3=N/C(=C\C(=O)O)C(=O)N3)nc(C)c2c1]

[2-(6-Ethoxy-4-methyl-quinazolin-2-ylamino)-5-oxo-
1,5-dihydro-imidazol-4-ylidene]-acetic acid Compound M9
Formula V(i)

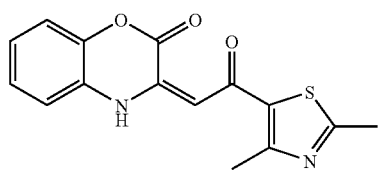 [SMILES: Cc1nc(C)c(C(=O)/C=C2/Nc3ccccc3OC2=O)s1]

3-[2-(2,4-Dimethyl-thiazol-5-yl)-2-oxo-
ethylidene]-3,4-dihydro-benzo[1,4]oxazin-2-one Compound M10
Formula V(j)

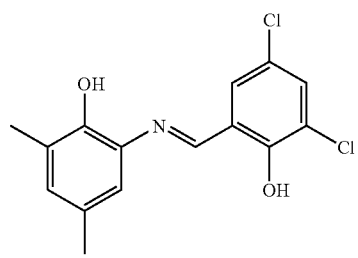 [SMILES: Cc1cc(C)c(O)c(/N=C/c2cc(Cl)cc(Cl)c2O)c1]

(E)-2,4-dichloro-6-((2-hydroxy-3,5-
dimethylphenylimino)methyl)phenol

Compound M11
Formula V(k)

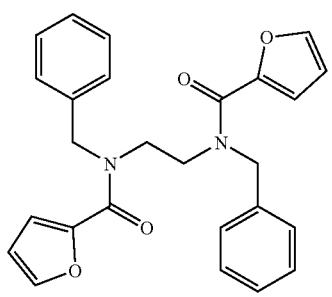 [SMILES: O=C(c1ccco1)N(CCN(Cc1ccccc1)C(=O)c1ccco1)Cc1ccccc1]

N,N'-(ethane-1,2-diyl)bis(N-benzylfuran-2-carboxamide)

TABLE 5-continued

Compound M14
Formula V(1)
aka C3
aka C6

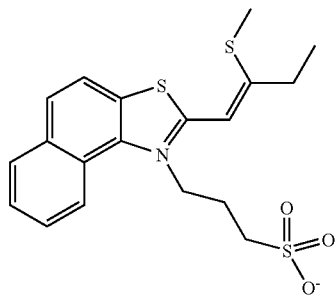

3-[2-(2-Methylsulfanyl-but-1-enyl)-
naphtho[1,2-d]thiazol-1-yl]-propane-1-sulfonic acid anion Compound M15
Formula V(m)
aka C5

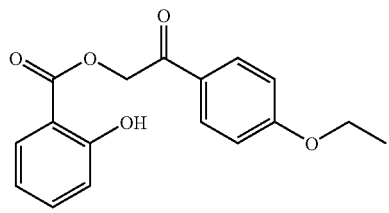 [SMILES: CCOc1ccc(C(=O)COC(=O)c2ccccc2O)cc1]

2-Hydroxy-benzoic acid 2-(4-ethoxy-phenyl)-2-oxo-ethyl ester

Compound M16
Formula V(n)

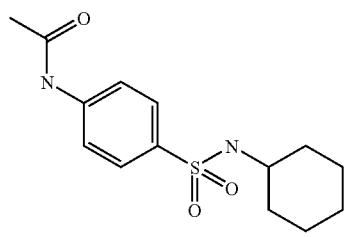 [SMILES: CC(=O)Nc1ccc(S(=O)(=O)NC2CCCCC2)cc1]

Compound M17
Formula V(o)
aka C3-6

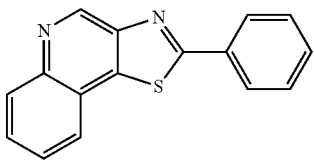 [SMILES: c1ccc(-c2nc3cnc4ccccc4c3s2)cc1]

2-Phenyl-thiazolo[4,5-c]quinoline

Compound M18
Formula V(p)

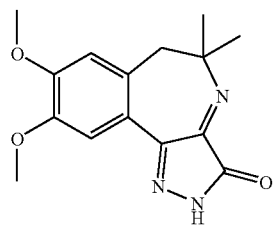 [SMILES: COc1cc2c(cc1OC)C1=NNC(=O)C1=NC(C)(C)C2]

8,9-Dimethoxy-5,5-dimethyl-5,6-dihydro-2H-
1,2,4-triaza-benzo[e]azulen-3-one

Compound M19
Formula V(q)

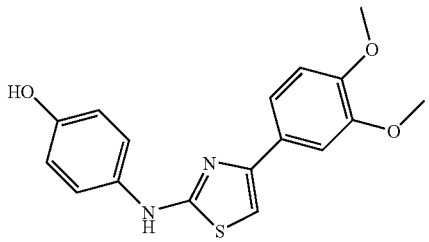 [SMILES: COc1ccc(-c2csc(Nc3ccc(O)cc3)n2)cc1OC]

4-[4-(3,4-Dimethoxy-phenyl)-thiazol-2-ylamino]-phenol

TABLE 5-continued

Compound M20
Formula V(r)

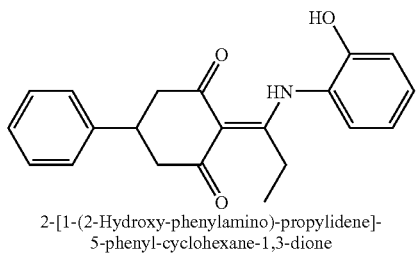

2-[1-(2-Hydroxy-phenylamino)-propylidene]-
5-phenyl-cyclohexane-1,3-dione

Compound M21
Formula V(s)

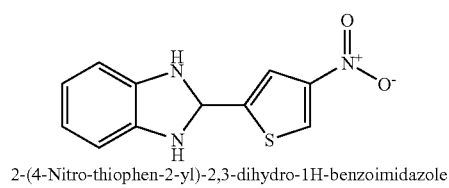

2-(4-Nitro-thiophen-2-yl)-2,3-dihydro-1H-benzoimidazole

Compound M22
Formula V(t)
aka C3-5

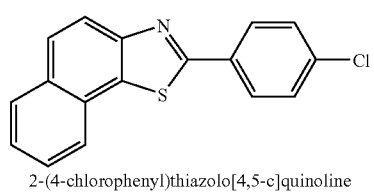

2-(4-chlorophenyl)thiazolo[4,5-c]quinoline

Compound M23
Formula V(u)

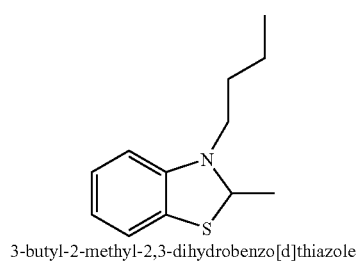

3-butyl-2-methyl-2,3-dihydrobenzo[d]thiazole

Each of the variables designated by, for example, R, X, Y, m, and n in any of the formulas disclosed herein can be selected independently. While we tend to use the term "compound(s)", we may also use terms like "agent(s)" to refer to the molecules described herein.

Definitions: The following definitions apply to the terms used in connection with any of the formulas herein. The term "halo" or "halogen" refers to any radical of fluorine, chlorine, bromine or iodine. The terms "cyclylalkyl" and "cycloalkyl" refer to saturated monocyclic, bicyclic, tricyclic, or other polycyclic hydrocarbon groups. Any atom can be substituted by, for example, one or more substituents. Cycloalkyl groups can contain fused rings, which share a common carbon atom. Cycloalkyl moieties can include, for example, cyclopropyl, cyclohexyl, methylcyclohexyl (the point of attachment to another moiety can be either the methyl group or a cyclohexyl ring carbon), adamantyl, and norbornyl.

The term "alkenyl" refers to a straight or branched hydrocarbon chain containing 2-20 carbon atoms and having one or more double bonds. Any atom can be substituted by one or more substituents. Alkenyl groups can include, for example, allyl, propenyl, 2-butenyl, 3-hexenyl and 3-octenyl groups. One of the double bond carbons can optionally be the point of attachment of the alkenyl substituent. The term "alkynyl" refers to a straight or branched hydrocarbon chain containing 2-20 carbon atoms and having one or more triple bonds. Any atom can be substituted by one or more substituents. Alkynyl groups can include, for example, ethynyl, propargyl, and 3-hexynyl. One of the triple bond carbons can optionally be the point of attachment of the alkynyl substituent.

The term "alkoxy" refers to an —O-alkyl radical. The term "heterocyclyl" refers to a monocyclic, bicyclic, tricyclic or other polycyclic ring system having: 1-4 heteroatoms if monocyclic; 1-8 heteroatoms if bicyclic; or 1-10 heteroatoms if tricyclic. The heteroatoms can be O, N, or S (e.g., carbon atoms and 1-4, 1-8, or 1-10 heteroatoms of N, O, or S if monocyclic, bicyclic, or tricyclic, respectively). The heteroatom can optionally be the point of attachment of the heterocyclyl substituent. Any atom can be substituted, by, for example, one or more substituents. The heterocyclyl groups can contain fused rings, which share a common carbon atom. Heterocyclyl groups can include, for example, tetrahydrofuranyl, tetrahydropyranyl, piperidinyl, morpholino, pyrrolinyl, and pyrrolidinyl.

The term "heteroaryl" refers to an aromatic monocyclic, bicyclic, tricyclic, or other polycyclic hydrocarbon groups having: 1-4 heteroatoms if monocyclic; 1-8 heteroatoms if bicyclic; or 1-10 heteroatoms if tricyclic. The heteroatoms can be O, N, or S (e.g., carbon atoms and 1-4, 1-8, or 1-10 heteroatoms of N, O, or S if monocyclic, bicyclic, or tricyclic, respectively). Any atom can be substituted by, for example, one or more substituents. Heteroaryl groups can contain fused rings, which share a common carbon atom. Heteroaryl groups include pyridyl, thienyl, furanyl, imidazolyl, and pyrrolyl.

The term "oxo" refers to an oxygen atom, which forms a carbonyl when attached to carbon, an N-oxide when attached to nitrogen, and a sulfoxide or sulfone when attached to sulfur.

The term "substituents" refers to a group "substituted" on, for example, an alkyl, cycloalkyl, alkenyl, alkynyl, aralkyl, heteroaralkyl, heterocyclyl, heterocycloalkenyl, cycloalkenyl, aryl, or heteroaryl group at any atom of that group. In one aspect, the substituents on a group are independently any one single, or any subset of, the aforementioned substituents. In another aspect, a substituent may itself be substituted with any one of the above substituents.

Salts, solvates, and other variants: The invention also encompasses pharmaceutically acceptable salts or solvates of a compound of any of Formulas I-IV or V(a)-V(u), and prodrugs, metabolites, structural analogs, and other pharmaceutically useful variants thereof. These other variants may be, for example, a complex containing the compound and a targeting moiety, as described further below, a second therapeutic agent or a detectable marker (e.g., the compound may incorporate a radioactive isotope or be joined to a fluorescent compound). When in the form of a prodrug, a compound may be modified in vivo (e.g., intracellularly) after being administered to a patient or to a cell in culture. The modified compound (i.e., the processed prodrug) may be identical to a compound described herein and will be biologically active or have enough activity to be clinically beneficial. The same is true of a metabolite; a given compound may be modified within a cell and yet retain sufficient biological activity to be clinically useful.

A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

Examples of prodrugs include esters and other pharmaceutically acceptable derivatives, which, upon administration to a subject, are capable of providing active compounds. A "prodrug" may be any pharmaceutically acceptable salt, ester, salt of an ester, or other derivative of a compound of this invention (for example an imidate ester of an amide), which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention may be modified by appending appropriate functionalities to enhance selected biological properties (e.g., targeting to a particular tissue). Such modifications are known in the art and include those which increase biological penetration into a given biological compartment (e.g., blood, lymphatic system, central nervous system), increase oral availability, increase solubility to allow administration by injection, alter metabolism and alter rate of excretion.

The compounds of the invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also contain linkages (e.g., carbon-carbon bonds) wherein bond rotation is restricted about that particular linkage (e.g., restriction resulting from the presence of a ring or double bond). Accordingly, all cis/trans and E/Z isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

As noted, the compounds of the invention may be mixed with or joined to a detectable marker or tag, to another therapeutic agent, or to a moiety that facilitates passage across the blood-brain barrier (see below).

Packaged products: The compounds described herein can be packaged in suitable containers labeled, for example, for use as a therapy to treat a disease or disorder characterized by protein aggregation or another form of undesirable association. The containers can include the compound (i.e., the diagnostic/prophylactic/therapeutic agent) and one or more of a suitable stabilizer, carrier molecule, flavoring, and/or the like, as appropriate for the intended use. Accordingly, packaged products (e.g., sterile containers containing one or more of the compounds described herein and packaged for storage, shipment, or sale at concentrated or ready-to-use concentrations) and kits, including at least one compound of the invention and instructions for use, are also within the scope of the invention. A product can include a container (e.g., a vial, jar, bottle, bag, or the like) containing one or more compounds of the invention and a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefore, and other uses. The compounds can be ready for administration (e.g., present in dose-appropriate units), and may include a pharmaceutically acceptable adjuvant, carrier or other diluent and/or an additional therapeutic agent. Alternatively, the compounds can be provided in a concentrated form with a diluent and instructions for dilution.

Stability: Combinations of substituents and variables envisioned by this invention are only those that result in the formation of stable compounds. The term "stable," as used herein, refers to compounds that are stable enough to allow manufacture and that maintain their integrity for a sufficient period of time to be useful for the purposes detailed herein (e.g., therapeutic or prophylactic administration to a subject).

Purity: In one aspect, the invention features substantially pure preparations of the compounds described herein or combinations thereof. A naturally occurring compound is substantially pure when it is separated to some degree from the compound(s) or other entities (e.g., proteins, fats, or minerals) it is associated with in nature. For example, a naturally occurring compound described herein is substantially pure when it has been separated from 50%, 60%, 70%, 75%, 80%, 85%, 90%, 95%, 96%, 97%, 98%, 99% or more of the compound(s) or other moieties it is associated with in nature. These degrees of purity are not limiting, however, the compounds of the invention need be only as pure as necessary to cause a beneficial clinical result and to conform with good manufacturing practices. While the compounds of the invention may be naturally occurring and may be purified using conventional techniques, they may also be non-naturally occurring and may be synthesized (naturally occurring compounds can be synthesized as well; see below). Compounds prepared by chemical synthesis are substantially pure, as are compounds that have been separated from a library of chemical compounds. A substantially pure compound may be one that is separated from all the other members of the compound library or it may be one that has been separated to a limited extent (e.g., it may remain associated with a limited number (e.g., 1, 2, 3, 4, or 5-10) of other members of the library. As noted, while more than one of the agents described herein can be formulated within the same composition, and while the compositions can also include a second therapeutic agent (as described herein), the pharmaceutical compositions of the invention expressly exclude extremely heterogeneous mixtures, such as libraries (e.g., combinatorial or compound libraries, including those that contain synthetic and/or natural products, and custom analog libraries, which may contain compounds based on a common scaffold). Such libraries can include hundreds or thousands of distinct compounds or random pools thereof. Whether or not commercially available, such libraries are excluded from the meaning of a pharmaceutical composition.

Formulations: Regardless of their original source or the manner in which they are obtained, the compounds of the invention can be formulated in accordance with their use. For example, the compounds can be formulated within compositions for application to cells in tissue culture or for administration to a patient. For example, the compounds can be mixed with a sterile, pharmaceutically acceptable diluent (such as normal saline). As noted below, and as known in the art, the type of diluent can vary depending upon the intended route of administration. The resulting compositions can include additional agents, such as preservatives. The compounds may also be applied to a surface of a device (e.g., a catheter) or contained within a pump, patch, or other drug delivery device. The therapeutic agents of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E. W. Martin), a well-known reference text in this field, and in the USP/NF (United States Pharmacopeia and the National Formularly).

A pharmaceutical composition (e.g., a composition containing a therapeutic agent or the DNA molecule encoding it) is formulated to be compatible with its intended route of administration. Examples of routes of administration include oral, rectal, and parenteral, for example, intravenous, intradermal, and subcutaneous, transdermal (topical), and transmucosal administration. Variants of the compounds described herein, formulated to cross the blood-brain barrier, are described below.

Diagnostic, prophylactic and therapeutic use: The compounds identified by the methods described herein (which may also be referred to herein as "therapeutic agents") may be used to treat a variety of disorders, including Huntington's disease. For example, the compounds described herein can be included as therapeutic agents in pharmaceutical compositions to treat HD and other conditions described herein that are mediated by (or characterized by) protein-protein association. The therapeutic agents of the invention can be used to treat any disease, disorder, or condition that results from an abnormal or undesirable association between two polypeptides (like or unlike). For example, the therapeutic agents of the invention can be used to treat neurodegenerative disorders (e.g., Huntington's Disease can be inhibited by inhibiting the association of huntingtin proteins) and disorders in which polyglutamine-containing transcription factors or coactivators are undesirably active (e.g., disorders (e.g., cancers) associated with homodimerization of jun or hexamerization of p53).

Treating a subject can encompass administration of a therapeutic agent as a prophylactic measure to prevent the occurrence of disease or to lessen the severity or duration of the symptoms associated with the disease. Physicians and others of ordinary skill in the art routinely make determinations as to the success or failure of a treatment. Treatment can be deemed successful despite the fact that not every symptom of the disease is totally eradicated. Treatment can also be deemed successful despite side-effects.

It is usual in the course of developing a therapeutic agent that tests of that agent in vitro or in cell culture are followed by tests in animal models of human disease, and further, by clinical trials for safety and efficacy in humans. Accepted animal models for many diseases are now known to those of ordinary skill in the art. For example, therapeutic agents of the present invention can be screened in a *Drosophila* model of neurodegeneration as well as in more evolutionarily advanced animals.

Mammalian models for Huntington's disease are available. To generate similar animal models, a homolog of the aggregation-disposed polypeptide is first cloned from the genome of the selected mammal using standard techniques. For example, the sequence can be amplified by PCR or obtained by screening an appropriate library under conditions of low stringency (as described, e.g., in Sambrook et al. supra.). Subsequently, trinucleotide repeats can be introduced into the gene by molecular cloning and mutagenesis techniques. For example, in a HD model, CAG repeats can be introduced in the HD gene. The site for insertion of the repeat sequence can be located by alignment of the cDNA from the desired mammal with the human cDNA for the aggregation-disposed protein. The modified gene with artificially expanded repeats can be reintroduced into the mammal using standard methods for transgenesis.

Methods for generating transgenic mice are routine in the art (See, e.g., Hogan et al., *Manipulating the Mouse Embryo*, Cold Spring Harbor Laboratory Press, Cold Spring Harbor, N.Y. (1994)). As an example, a mouse bearing a transgene comprising the HD gene and expanded CAG repeats has symptoms similar to the human disease. Murine symptoms can include hyperactivity, circling, abnormal gait, tremors, learning deficits, hypoactivity, and hypokinesis. Neuropathological symptoms include general brain atrophy, progressive striatal atrophy, neuropil aggregates, inclusions in the striatum, reduced dendritic spines, cell loss in the cortex, and striatum.

Any of these behavioral or physiological deficits can be assessed in order to determine the efficacy of a given therapeutic agent of the invention. For example, the agent can be administered to a transgenic mouse model, generated as described above. The symptoms of a treated mouse can be compared to untreated mice at various times during and after treatment. In addition, treated and untreated mice can be sacrificed at various intervals after treatment, and the neuropathology of the brain can be analyzed. Thus, the efficacy of the treatment can be evaluated readily by comparing the behavioral symptoms, neuropathological symptoms, and clinical symptoms of treated and untreated mice.

In specific embodiments, the compositions of the present invention can be administered to a subject having any disease mediated by (or characterized by) an abnormal or unwanted association of one protein with another. Examples include immunoglobulin light chain amyloidosis, HD, Parkinson's disease, adult-onset diabetes, cirrhosis (e.g., cirrhosis of the liver), emphysema, or a prion disease, such as Creutzfeldt-Jakob disease. Other conditions that can be treated or prevented with one or more of the compounds of the present invention include amyotrophic lateral sclerosis, dentatorubral pallidoluysian atrophy, spinal bulbar muscular atrophy (SBMA; also known as Kennedy's disease), any of the several types of spinocerebellar ataxias (e.g., SCA1, SCA2, SCA6, SCA7 and Machado-Joseph disease (MJD/SCA3)), dentatorubral-pallidoluysian atrophy, and disorders in which polyglutamine-containing transcription factors or coactivators are undesirably active (e.g., disorders associated with homodimerization of jun or hexamerization of p53). For example, a subject may have been diagnosed as having, or at risk for developing, a carcinoma (e.g., breast cancer), amyloidosis, a myeloma, kuru, a neuroblastoma, cystic fibrosis, an alpha-1-antitrypsin deficiency disease, or a disorder with a similar underlying cellular basis (i.e., an association with undesirable (e.g., excessive or insufficient) protein-protein aggregation, dimerization, or other interaction).

The synuclein proteins (alpha, beta and gamma synuclein) have been implicated in Parkinson's disease and breast cancer, and are targets for the compositions of the invention. As targets, these proteins can be incorporated in the screening assays described herein. Proteins such as amyloid light chains and amyloid-associated proteins, which are associated with amyloidosis, can also be targeted by the compositions and methods of the invention. Other aggregation- or association-disposed polypeptides include: mutant transthyretin, which is associated with familial amyloid polyneuropathies; beta2 microglobulin, aggregation of which causes complications during chronic renal dialysis; immunoglobulin light chain, which is associated with multiple myelomas and various other B-cell proliferations; prion proteins, which cause spongiform encephalopathies such as Creutzfeldt-Jakob disease and kuru in humans; cystic fibrosis transmembrane conductance regulator (CFTR), which is a hallmark of cystic fibrosis; p53, which has been observed to aggregate in some neuroblastomas, carcinomas, and myelomas; and alpha-1-antitrypsin, which aggregates in patients with alpha-1-antitrypsin deficiency disease.

Subjects who are treated with the compounds of the invention may have been diagnosed with any disease characterized by aberrant or undesirable association between proteins, whether that association occurs to a greater or lesser extent than is normal (in, e.g., a healthy patient) or desirable. Alternatively, the subject may be at risk for developing these disorders. For example, a subject may have a family history or a genetic mutation or element (e.g., an expanded trinucleotide repeat) that contributes to the development of disease. Human subjects, in consult with their physicians and/or other health care professionals, can decide whether their risk is great enough to undergo preventative care (as is the case for any prophylactic treatment or procedure). While the subjects of the preventative and/or therapeutic regimes described herein may be human, the compounds and compositions of the invention can also be administered to non-human subjects.

The prophylactic and therapeutic methods can be carried out by administering to the subject a pharmaceutical composition containing a therapeutically effective amount of one or more of the compounds described herein. While a single compound may be effective, the invention is not so limited. A subject can be treated with multiple compounds, administered simultaneously or sequentially. For example, a subject can be treated with one or more of the compounds described herein and, optionally, a chemotherapeutic agent, an analgesic, a bronchodilator, levodopa or a similar medication. The combination therapy will, of course, depend on the disorder being treated. Where a compound of the invention is administered to treat a patient with a cancer, it may be combined with a known chemotherapeutic agents used to treat that type of cancer; where a compound of the invention is administered to treat a patient with Parkinson's disease, it may be combined with a medication to increase dopamine levels in the brain; and so forth.

Compounds that mediate association between proteins can also be used to diagnose diseases characterized by protein aggregation (or, as noted above, other undesirable interaction (e.g., dimerization or complex formation)). These methods can be carried out by providing a biological sample from a patient suspected of having a disease associated with an abnormal or undesirable association between proteins; exposing the sample to a compound of the invention; and determining whether the compound modulates the association of proteins within the sample. The compound can be one that is known to interact directly with a primary target or one that modulates protein-protein interaction by acting upstream from the primary target. The compound can also be one that is known to interact with proteins in the context of the suspected disease. For example, a compound that is known to inhibit the aggregation of Huntingtin can be used to diagnose a patient suspected of having HD. The sample will be exposed to the compound for a time and under conditions (e.g., physiological conditions of temperature and pH) sufficient to permit the compound to affect proteins within the sample (e.g., Huntingtin, tau, or Aβ proteins within cells within the sample). The diagnostic methods can be carried out before, after, or in conjunction with other diagnostic tests, and their results can inform the subject's treatment regime. For example, where a compound is found to modulate the aggregation of Huntingtin proteins in a sample obtained from a patient suspected of having HD, that compound may then be used to treat the patient.

The blood-brain barrier is an obstacle for the delivery of drugs from circulation in the bloodstream to the brain. The endothelial cells of brain capillaries are connected by tight intercellular junctions, which inhibit the passive movement of compounds out of the blood plasma into the brain. These cells also have reduced pinocytic vesicles in order to restrict the indiscriminate transport of materials intracellularly. These features of the brain regulate the exchange of materials between plasma and the central nervous system. Both active and passive transport mechanisms operate to exclude certain molecules from traversing the barrier. For example, lipophilic compounds are more permeable to the barrier than hydrophilic compounds (Goldstein et al., *Scientific American* 255: 74-83, 1996; Pardridge et al., *Endocrin. Rev.* 7:314-330, 1996).

However, the blood-brain barrier must also allow for the selective transport of desired materials into the brain in order to nourish the central nervous system and to remove waste products. The mechanisms by which this is accomplished can provide the means for supplying the therapeutic agents described herein.

The compositions of the invention can be delivered to the CNS following conjugation with other compounds as follows (and as described further in, for example, U.S. Pat. No. 5,994,392). In one instance, polar groups on a compound are masked to generate a derivative with enhanced lipophilic qualities. For example, norepinephrine and dopamine have been modified with diacetyl and triacetyl esters to mask hydroxyl groups. An implementation of this strategy has been previously used to create a pro-drug derivative of dopamine (see U.S. Pat. No. 5,994,392). The modified drugs are generally referred to as pro-drugs, and the compounds of the invention encompass those described herein in which polar groups are masked. This method may have the additional advantage of providing an inactive species of the compound in the general circulation. After crossing the blood-brain barrier, enzymes present in the central nervous system are able to hydrolyze the linkages (e.g., ester linkages), thereby unmasking the compound and liberating the active drug. Thus, compounds of the invention can be chemically modified to create pro-drugs by, e.g., conjugation to a lipophilic moiety or carrier. A compound or a variant thereof having at least one free hydroxyl or amino group can be coupled to a desired carrier (e.g., a fatty acid, a steroid, or another lipophilic moiety).

More specifically, and for example, the hydroxyl groups can first be protected with acetonide. The protected agent is then reacted with the desired carrier in the presence of a water-extracting compound (e.g., dicyclohexyl carbodiimide), in a solvent (e.g., dioxane, tetrahydrofurane), or N,N dimethylformamide at room temperature. The solvent is then removed, and the product is extracted using methods routinely used by those of ordinary skill in the art. Amine groups can be coupled to a carboxyl group in the desired carrier. An amide bond is formed with an acid chloride or low carbon ester derivative of the carrier. Bond formation is accompanied by HCl and alcohol liberation. Alcohol groups on the compound can be coupled to a desired carrier using ester bonds by forming an anhydride derivative, i.e. the acid chloride derivative, of the carrier. One of ordinary skill in the art of chemistry will recognize that phosphoramide, sulfate, sulfonate, phosphate, and urethane couplings are also useful for coupling a therapeutic agent (e.g., a compound described herein) to a desired carrier. A useful and adaptable method for lipidation of antibodies is described by Cruikshank et al. (*J. Acquired Immune Deficiency Syndromes and Human Retrovirology* 14:193, 1997).

Procedures for delivering therapeutic agents (or "compounds") of the invention to the CNS can also be carried out using the transferrin receptor as described, for example, in U.S. Pat. No. 6,015,555. To implement this procedure, the agents are conjugated to a molecule that specifically binds to the transferrin receptor (e.g., an antibody or antigen-binding fragment thereof, or transferrin). Methods for obtaining antibodies against the transferrin receptor and for coupling the antibodies to a desired compound are also described in U.S. Pat. No. 6,015,555.

Monoclonal antibodies that specifically bind to the transferrin receptor include OX-26, T58/30, and B3/25 (Omary et al., *Nature* 286888-891, 1980), T56/14 (Gatter et al., *J. Clin. Path.* 36:539-545, 1983), OKT-9 (Sutherland et al., *Proc. Natl. Acad. Sci. USA* 78:4515-4519, 1981), L5.1 (Rovera, *Blood* 59:671-678, 1982) and 5E-9 (Haynes et al., *J. Immunol.* 127:347-351, 1981). In one embodiment, the monoclonal antibody OX-26 is used. The antibody of choice can be an Fab fragment, a F(ab')$_2$ fragment, a humanized antibody, a chimeric antibody, or a single chain antibody.

The antibody to the transferrin receptor is conjugated to a desired compound with either a cleavable or non-cleavable linker. The preferred type of linker can be determined without undue experimentation by making cleavable and non-cleavable conjugates and assaying their activity in, for example, an in vitro or cell culture assay described herein. The conjugates can be further tested in vivo (e.g., in a animal model of a disease of interest). Examples of chemical systems for generating non-cleavable linkers include the carbodiimmide, periodate, sulfhydryl-maleimide, and N-succinimidyl-3-(2-puridyldithio) propionate (SPDP) systems. Carbodiimide activates carboxylic acid groups, which then react with an amino group to generate a noncleavable amide bond. This reaction may be especially useful for coupling two proteins. Periodate is used to activate an aldehyde on an oligosaccharide group such that it can react with an amino group to generate a stable conjugate. Alternatively, a hydrazide derivative of the desired compound can be reacted with the antibody oxidized with periodate. Sulfhydryl-maleimide and SDPD use sulfhydryl chemistry to generate non-cleavable bonds. SDPD is a heterobifunctional crosslinker that introduces thiol-reactive groups. In the sulfhydryl-maleimide system, an NHS ester (e.g., gamma-maleimidobutyric acid NHS ester) is used to generate maleimide derivative, for example, of a protein drug or antibody. The maleimide derivative can react with a free sulfhydryl group on the other molecule.

Cleavable linkers are also useful. Cleavable linkers include acid labile linkers such as cis-aconitic acid, cis-carboxylic alkadienes, cis-carboxylic alkatrienes, and polypeptide-maleic anhydrides (see U.S. Pat. No. 5,144,011).

In one embodiment, the compound is a compound having one of the structures shown in Tables 1-5. Such a compound can be covalently attached to an antibody specific for the transferrin receptor. In one embodiment, use of a single chain antibody is preferred in order to facilitate covalent fusion with the therapeutic agent.

The targeting antibody can be linked covalently to the therapeutic agent (or "compound") of the invention. A protease recognition site can be included in the linker if cleavage of the antibody is required after delivery.

The efficacy of strategies to deliver a desired compound across the blood-brain barrier can, of course, be monitored. The desired compound, conjugated for delivery across the blood-brain barrier, is administered to a test mammal (e.g., a rat, a mouse, a non-human primate, a cow, a dog, a rabbit, a cat, or a sheep). One of ordinary skill in the art will, however, recognize that the permeability of the blood-brain barrier varies from species to species, with the human blood-brain barrier being the least permeable. The mode of administration can be the same as the desired mode of treatment (e.g., intravenous). For a comprehensive analysis, a set of test mammals is used. The test mammals are sacrificed at various times after the agent is administered and are then perfused through the heart with, e.g., Dulbecco's phosphate-buffered saline (DPBS) to clear the blood from all organs. The brain is removed, frozen in liquid nitrogen, and subsequently sectioned in a cryostat. The sections are placed on glass microscope slides. The presence of the desired agent is then detected in the section, for example with an antibody, or by having administered a radiolabeled or otherwise tagged compound (such labeled therapeutic compounds as described above). Detection is indicative of the compound having successfully traversed the blood-brain barrier. If a method of enhancing the compounds permeability to the blood-brain barrier is being assessed, then the amount of the agent detected in a brain section can be compared to the amount detected in a brain section from an animal treated with the same compound without the enhancing method.

The terms "blood-brain barrier permeant" or "blood-brain barrier permeable" are qualities of a compound for which the ratio of a compound's distribution at equilibrium in the cerebrospinal fluid (CSF) relative to its distribution in the plasma (CSF/plasma ratio) is greater than at least (or about) 0.01, 0.02, 0.05, or 0.1. While lower ratios are generally preferred, any ratio that allows a compound to be used clinically is acceptable.

To facilitate targeting to a polypeptide of interest (e.g., to a Huntingtin or jun protein), the compound (e.g., a compound conforming to any of Formulas I IV or V(a) V(u)) can include a moiety that specifically binds to the target protein. For example, a compound conforming to Formula I can be joined to an antibody or an antigen-binding portion thereof (e.g., a single chain antibody) that specifically binds the target protein (e.g., Huntingtin or jun). Targeting moieties are described further below.

A therapeutic vector can be administered to a subject, for example, by intravenous injection, by local administration (see U.S. Pat. No. 5,328,470) or by stereotactic injection (see e.g., Chen et al., *Proc. Natl. Acad. Sci. USA* 91:3054-3057, 1994). The compound can be further formulated, for example, to delay or prolong the release of the active agent by means of a slow release matrix.

Regardless of whether or not the compound is to cross the blood-brain barrier, it can be conjugated to a targeting agent that facilitates interaction with a target protein (e.g., Huntingtin or jun). As noted, the compound can be directly or indirectly joined to an antibody (e.g., a single chain antibody) or an antigen-binding fragment thereof that specifically binds the target protein.

An appropriate dosage of the therapeutic agents of the invention must be determined. An effective amount of a therapeutic compound is the amount or dose required to ameliorate a symptom of a disorder associated with protein aggregation, such as a disorder characterized by a trinucleotide repeat expansion. Determining the amount required to treat a subject is routine to one of ordinary skill in the art (e.g., a physician, pharmacist, or researcher). First, the toxicity and therapeutic efficacy of an agent (i.e. a tri-domain molecule) is determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Compounds, formulations, and methods of administration with high therapeutic indices are preferable as such treatments have little toxicity at dosages that provide high efficacy. Compounds with toxic or undesirable side effects can be used, if means are available to deliver the compound to the affected tissue, while minimizing damage to unaffected tissue.

In formulating a dosage range for use in humans, the effective dose of a therapeutic agent can be estimated from in vitro cell studies and in vivo studies with animal models. If an effective dose is determined for ameliorating a symptom in cell culture, a dose can be formulated in an animal in order to achieve a circulating plasma concentration of sodium butyrate that falls in this range. An exemplary dose produces a plasma concentration that exceeds the $IC_{50}$ (i.e., the concentration of the test compound which achieves a half-maximal inhibition of symptoms) as determined in cell culture assays. The circulating plasma concentration can be determined, for example, by administering a labeled therapeutic composition to the test animal, obtaining a blood sample, and quantitating the amount of labeled compound present at various times after administration.

An appropriate daily dose of a therapeutic agent can be between about 0.1 mg/kg of body weight to about 500 mg/kg, or between about 1 mg/kg to about 100 mg/kg. The dose can be adjusted in accordance with the blood-brain barrier permeability of the compound. For example, a therapeutic compound can be administered at a dosage of 50 mg/kg to 100 mg/kg in order to treat the brain. The dose for a patient can be optimized while the patient is under care of a physician, pharmacist, or researcher. For example, a relatively low dose of a tri-domain therapeutic can be administered initially. The patient can be monitored for symptoms of the disorder being treated (e.g., HD). The dose can be increased until an appropriate response is obtained. In addition, the specific dose level for any particular subject can vary depending on the age, body weight, general health, gender, and diet of the subject, the time of administration, the route of administration, the rate of excretion, and other drugs provided in combination.

As occurs in the course of all drug development, optimal treatment regimes will emerge through further modeling and clinical trials. It may be, for example, that a patient will receive a combination of compounds that act synergistically to inhibit polypeptide association by the same or different mechanisms of action. Combination therapies may also rely on administration of a compound that interferes with gene transcription (e.g., a small molecule or a nucleic acid that mediates RNAi) and a compound that facilitates degradation of any remaining unwanted polypeptide-containing complexes.

The efficacy of a dose of any therapeutic agent can be determined in a subject. For example, the subject can be monitored for clinical symptoms, for example, a symptom of a trinucleotide repeat disease, such as a symptom of HD. Behavioral symptoms of HD include irritability, apathy, lethargy, depression, hostile outbursts, loss of memory and/or judgment, loss of ability to concentrate, anxiety, slurred speech, difficulty swallowing and/or eating, and inability to recognize persons. Clinical symptoms of HD include loss of coordination, loss of balance, inability to walk, uncontrolled movements of the fingers, feet, face, and/or trunk, rapid twitching, tremors, chorea, rigidity, and akinesia (severe rigidity).

Methods of making: The compounds of the invention or biologically active variants thereof (e.g., salts) may be synthesized in vitro, produced in vivo (e.g., produced within the body (e.g., intracellularly) following administration to a patient), or produced following application to a cell in culture. Accordingly, the present invention features methods of making the compounds and compositions of the present invention. The compounds can be synthesized using routine techniques known to one of ordinary skill in the art. For example, the compounds can be made by providing a starting compound or intermediate and reacting the compound or intermediate with one or more chemical reagents in one or more steps to produce a compound described herein (e.g., a compound of any of Formulas I-IV or V(a)-V(u)).

Some of the compounds described herein can be obtained from commercial sources. As noted, others can be synthesized by conventional methods using commercially available starting materials and reagents. The compounds described herein can be separated from a reaction mixture and further purified by a method such as column chromatography, high-pressure liquid chromatography, or recrystallization. As can be appreciated by one of ordinary skill in the art, further methods of synthesizing the compounds of the formulae herein are available. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. Techniques useful for the separation of isomers, for example, stereoisomers are within skill of the art and are described in Eliel, E. L.; Wilen, S. H.; Mander, L. N. Stereochemistry of Organic Compounds, Wiley Interscience, NY, 1994. For example compounds can be resolved via formation of diasteromeric salts, for example, with a chiral base, for example, (+) or (−) a-methylbenzylamine, or via high performance liquid chromatography using a chiral column.

Platform and scaffold use: In an alternate embodiment, the compounds described herein may be used as platforms or scaffolds that may be utilized in combinatorial chemistry techniques for preparation of derivatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., "Solid-Supported Combinatorial and Parallel Synthesis of Small-Molecular-Weight Compound Libraries", Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60, 1997). Thus, one embodiment relates to methods of using the compounds described herein for generating derivatives or chemical libraries. The methods can be carried out by performing these, and optionally additional, steps: (1) providing a body comprising a plurality of wells; (2) providing one or more compounds identified by methods described herein in each well (e.g., any of the compounds of Formulas I-IV or V(a)-V(u); (3) providing an additional one or more chemicals in each well, where the compound, upon exposure to the chemical(s) may produce one or more products; and (4) isolating the resulting one or more products from each well. We may refer to the original compound as the "first" compound and to the chemical as the "second" compound. The order in which the first and second compounds are added to the wells can vary, and the methods can be carried out in vitro or in cell culture. Lead derivatives can be further tested in animal models.

In alternate embodiments, the methods of using the compounds described herein for generating derivatives or chemical libraries can be carried out using a solid support. These methods can be carried out by, for example: (1) providing one or more of the compounds described herein attached to a solid support; (2) treating the one or more compounds identified by methods described herein attached to a solid support with one or more additional compounds or chemicals; (3) isolating the resulting one or more products from the solid support. In these methods, "tags" or identifier or labeling moieties may be attached to and/or detached from the compounds described herein or their derivatives, to facilitate tracking, identification or isolation of the desired products or their intermediates. Such moieties are known in the art and exemplary tags are noted above. The chemicals (or "second" compound(s)) used in the aforementioned methods may include, for example, solvents, reagents, catalysts, protecting group and deprotecting group reagents, and the like. Examples of such chemicals are those that appear in the various synthetic and protecting group chemistry texts and treatises which are known in the art and may be referenced herein.

Databases: In one aspect, the invention includes cell-based and in vitro assays (e.g., high throughput screens) that can be used with essentially any compound collection. Following an assay, the result can be recorded in a database, and such databases are also within the scope of the present invention. For example, the invention features a computer-readable database that includes a plurality of records. Each record includes (a) a first field that includes information reflecting the identity of an agent (e.g., an agent within one of the types of libraries described herein) and (b) a second field that includes information concerning the impact of the agent on polypeptide association. Additional fields may include the results of toxicity tests, dose-response tests, and the like. The information contained with the fields can be obtained in any order (e.g., the information reflecting protein association can be obtained first). However, to help ensure the integrity of the database, the information should be obtained independently (or "blindly"). The database can also include a field comparing the agent to a clinical outcome (e.g., an improvement in a sign or symptom associated with Parkinson's disease, Huntington's disease, cancer, or any of the other disorders described herein). The number of records can be, but is not necessarily, great. For example, a useful database can include at least 10, 25, 50, 100, 250, 500, 1000, 1500, 1800, 2000, or 2500 records.

The invention is further illustrated by the following examples, which should not be construed as further limiting.

EXAMPLES

Example 1

Effect of Expanded Polyglutamine (PolyQ) on Cell Growth and Protein Aggregation

We expressed sequences encoding fragments of the huntingtin gene having either an expanded region of glutamine residues (104Q) or a normal length (25Q) in the yeast *S. cerevisiae*. We fused the genes for 104Q and 25Q to the DNA sequence encoding green fluorescent protein to allow microscopic detection of the corresponding polypeptide in vivo. Both genes also contained a short sequence corresponding to the FLAG-tag at the N-terminus. We expressed the 104Q and 25Q transgenes in yeast under the regulation of a Gal1 promoter. Upon transfer of the cells to a galactose-containing medium, 104Q formed multiple aggregates (10-20 per cell) in the cytoplasm within 4-6 hours, while 25Q was soluble. While 25Q-GFP had no effect on the growth rate of the cells, 104Q expression caused a general cessation of growth. With time, expression of 104Q strongly declined and yeast growth was partially restored, but at a very low rate. The presence of FLAG-tag in the 104Q sequence may be critical for growth cessation.

Example 2

A Screen for Genes that Modulate the Toxicity of PolyQ-Containing Polypeptides and Formation of Inclusion Bodies We performed a screen for yeast genes involved in polyQ aggregation by identifying suppressors of the polyQ-dependent growth defect. A number of mutant clones expressing 104Q formed large colonies (i.e., clones in which the growth defect was suppressed) and were selected for further analysis. In some of these colonies, aggregation of 104Q was strongly inhibited, while in others, aggregation was normal. Three clones that demonstrated suppressed aggregation were analyzed. About 85% of the cells in these clones did not have inclusion bodies at all, while about 15% of the cells had one large aggregate. Notably, expression levels of 104Q in these mutants were much higher than in the parental wild type, and reached the levels of expression of 25Q. Increased expression of 104Q in the mutants closely correlated with increased fluorescence. We identified mutations in these clones by complementation analysis, which showed the mutations to be in the HSP 104 gene. Precise deletion of the gene hsp104 led to suppression of the growth defect caused by 104Q, prevented aggregation of this polypeptide, and allowed its high expression. Mutations in ssa1, ssa2, and ydj1 genes also affected 104Q aggregation but caused very different phenotypes. Many more inclusion bodies were formed in these mutants, but they were much smaller than in the wild type, and the fraction of 104Q in these inclusion bodies was very low. Similar to the hsp104 mutation, ssa1, ssa2, and ydj1 mutations cause a reduced formation of inclusion bodies and also suppressed the growth defect caused by the extended polyQ domain. Based on these data, we established a simple screen to identify mammalian genes that inhibit formation of aggregates when overexpressed. An expression library of mammalian genes from HeLa cells was transfected into 104Q-GFP-expressing yeast cells and large clones (i.e., those in which growth defect was suppressed), were selected. Out of about 30,000 colonies screened, 21 colonies demonstrated suppression of the growth defect. Many of the plasmids were found to be "false positives" since they were unable to suppress the growth defect after isolation and re-transforming into a different 104Q-expressing clone. Two plasmids (each present in several selected clones) encoding mammalian genes partially suppressed 104Q aggregation. These plasmids caused phenotypes similar to those of cells carrying mutations in the Hsp70 or DnaJ genes. Sequencing of these genes revealed that one encoded the chaperonin TCP1α, and another encoded an unknown ORF. This genetic approach can provide insight to the mechanisms driving formation of inclusion bodies, and can identify potential targets for design of drugs that affect aggregation of proteins, such as the polyQ-containing proteins described above.

Example 3

Screening of Chemical Compound Libraries

We designed a screen for chemical compounds that can affect protein aggregation. The screen was designed based on the phenotypical differences between cells expressing 104Q and 25Q. The phenotypes included difference in growth rate and in fluorescence levels. We used microtiter plates to screen chemical libraries by the described method. We grew yeast transformed with either the 104Q-, or the 25Q-encoding plasmids separately in liquid medium in the presence of glucose, which inhibits polyQ expression. In the mid-log phase of growth, we washed the cells to remove glucose and resuspended them in a medium containing galactose, which induces polyQ expression. We placed the cell suspensions in 96- or 348-well plates and incubated them with aeration at 30° C. for 20 hours. We then measured cell density and fluorescence using a plate reader. Very little increase in the culture density and fluorescence was seen with cells expressing 104Q, but both parameters increased strongly for cells expressing 25Q. In general, an approximately 3-5 fold difference in cell number, and an approximately 20-30 fold difference in fluorescence was observed in 104Q and 25Q cultures. Compounds from a chemical library were added to 104Q culture right after plating into the microtiter plates. Compounds that enhanced cell growth or fluorescence were selected. These compounds were then tested for the ability to reduce aggregation of 104Q. Thirteen compounds were found to either enhance growth or reduce aggregation of cells expressing 104Q, or cause both effects. These compounds were then tested for the ability to reduce aggregation of 104Q in cells of the neuron-derived PC12 cell line. The compounds identified by this method are leads for development of drugs for treatment of diseases related to expansion of polyQ.

Example 4

Screening Method for Using an Epitope Tagged PolyQ Peptide in a Screen for Compounds that Inhibit Protein Aggregation An epitope-tagged polyQ peptide can be used to screen for, and thereby identify, compounds that modulate (e.g., inhibit) protein aggregation or another type of association between proteins. For example, cells can be plated on UV-treated coverslips in a 2 cm 6-well plate and incubated overnight in 2 ml 10% serum containing DME media. The next day, the cells are transiently transfected with 1-2 µg of DNA plasmid encoding a myc-tagged polyQ polypeptide using the lipofection reagent, Transfectam® (Promega, Madison, Wis.), following the Promega standard protocol. After 48 hours, the cells are washed twice in PBS, fixed in 2% formaldehyde for 10 minutes, treated for five minutes with 0.1% Triton-X (to permeabilize the cells), then incubated in a humidified chamber with PBS with 10% goat serum and 0.2% Tween-20. Following incubation, the cells can be visualized with an anti-myc fluorescent antibody (Cy3, rhodamine and FITC are commonly used fluorophores, FLAG; myc and HA are common epitope tags); and analyzed for inhibition of aggregation using high magnification fluorescent microscopy. The examination, whether the assay is configured as described here or as described elsewhere herein, can be carried out by eye or automated. For example, a microscope stage can be automatically moved (by, for example, a robotic device) so that each well appears beneath the lens and is photographed. A computer attached to the microscope can receive and analyze the data.

Example 5

Screen to Identify Transcriptional Repressors and Activators, and Compounds Facilitating Degradation of Extended polyQ High sensitivity of R2/6 cell lines to chemical treatment was used as a basis for a high-throughput screen of 30,000 compounds. The purpose of the screen was to identify transcriptional repressors, such as cystamine and C9 (A33 in Table 1), transcriptional activators, and compounds facilitating degradation of extended polyQ.

The compound C9 (aka C4-DAK) down-regulated expression of a mutant Huntingtin transgene (htt) in ecdyson-based inducible PC12 cells and down-regulated expression of htt and SOD1 transgenes (implicated in ALS) in transiently transfected HeLa cells. The compound C9 (A33 in Table 1) has structural similarity to the histone deacetylase (HDAc)

inhibitor, scriptaid (6-(1,3-Dioxo-1H,3H-benzo[de]isoquinolin-2-yl)-N-hydroxyhexanamide) (Su et al., *Cancer Res.* 60:3137, 2000; A5 in Table 1). We observed the most dramatic effect on expression level by C9 and scriptaid in the PC12 cell line 14A2/6 expressing the extended polyQ mutant htt(104Q). The effect of C9 on the down-regulation of polyQ expression, was similar to cystamine, a drug that has shown efficacy in a mouse model for Huntington's Disease (HD). Cystamine blocked protein aggregation and prolonged the survival of R2/6 HD mice by an unknown mechanism. Both C9 and cystamine reversed the stimulatory effect of the HDAc inhibitor, scriptaid, on expression and aggregation in PC12 cells. 14A2/6 cells were at least 5-fold more responsive to chemical treatment than other cell lines tested. 2.5 µM of Scriptaid in a media caused dramatic overexpression of a transgene, aggregation in 100% of the cells, and cell death of 14A2/6 cells. In other cell lines, the same concentration of Scriptaid only modestly stimulated the expression of the transgene. Both cystamine and C9 rescued PC12 cells from scriptaid-dependent synthetic lethality, whereas the other blockers of aggregation failed to reverse the effect of scriptaid on transgene expression or PC12 cell death.

Example 6

A Screen for Small Molecule Inhibitors of Protein Aggregation

In the study that follows, we identified and characterized small chemical molecules that inhibit protein association by screening a library of 16,000 such molecules. We used a yeast-based assay for aggregation, and selected nine structurally diverse inhibitors. We found that four of these molecules suppressed protein association well in mammalian cells in vivo but not in vitro. This suggests that the molecules either depend on metabolic conversion to become inhibitors or inhibit aggregation indirectly, targeting cellular pathway(s) of protein aggregation that are active in whole animals. In view of these four compounds, we synthesized more than 100 structural analogs and tested them in cell culture to select the compounds most effective in inhibiting aggregation. We studied the effects of the most potent compounds on polyQ aggregation in neurons in brain slices isolated from HD transgenic mice and maintained in vitro.

For our high throughput screen, we developed a novel yeast model of polyglutamine aggregation using an amino-terminal fragment of mutant HD protein (Htt) containing extended polyglutamines (103Q). This mutant efficiently aggregates in cells and causes cytotoxicity.

For the compound screen, we engineered the Erg6 yeast strain to express the "103Q" polypeptide tagged with EGFP under the control of a GAL1 promoter. This strain, engineered as described here, is within the scope of the present invention. The erg6 mutation inhibits ergosterol biosynthesis, which enhances membrane fluidity and results in increased membrane permeability to a variety of chemical compounds. The yeast culture was grown to mid-logarithmic phase, shifted to galactose medium to induce 103Q expression, placed in 96-well plates, and supplemented with compounds. We used the optical density at 600 nm to monitor yeast growth and fluorescence in FITC channel to monitor expression levels of 103Q-GFP fusion polypeptides. From the screened compounds, we selected chemical compounds that caused an increase in growth and/or an increase in fluorescence. The ability of pre-selected compounds to suppress 103Q aggregation was examined microscopically, and we identified nine inhibitors of aggregation from the library screened (from Diverse Set collection, ChemBridge Corp., San Diego, Calif.).

To study the inhibitors we identified using the yeast screen in mammalian cells, we employed ecdyson-inducible rat phaeochromocytoma (PC12) cells. Compounds were tested in two clones, 14A2/5 and 14A2/6, with highest aggregation rate. We incubated undifferentiated PC12 cells with muristerone A to induce 103Q expression, and we exposed the cells to compounds at concentrations ranging from 1 to 10 µM. Four compounds, including C1 (A16 in Table 1), C2 (B1 in Table 2), C3 (M14 in Table 5), and C4 (A2 in Table 1), showed significant inhibitory effects on aggregation of 103Q in the two PC12 clones tested. Under the test conditions, the $IC_{50}$ for compound C1 was 10 µM; for compounds C2 and C3, it was 5 µM; and for compound C4 it was 2.5 µM. All compounds were non-toxic except C2, which was toxic at concentrations higher than 5 µM.

The inhibitory activity we observed with C1-C4 in the PC12 cell model described above was confirmed in Cos1 cells transiently transfected with a CMV promoter-based DNA construct that encodes an Htt exon I fragment of Huntington's disease protein (Htt)) having 51 consecutive glutamine residues (HD Q51). When expressed in Cos1 cells, HD 51Q polypeptides readily form aggregates. Transfected Cos1 cells were incubated with C1-C4 compounds in culture medium and lysed. The lysates were then heat-denatured in SDS and passed through a cellulose acetate membrane, which captures aggregated, but not soluble polypeptides. Polyglutamine aggregates trapped on membranes were detected by immunostaining with antibody specific to extended polyQ. Pre-incubation of cells with compounds C1, C3, and C4 decreased the amount of retained polyQ, indicating inhibitory effects on polyQ aggregation. The $IC_{50}$ for compound C1 was 10 µM and the $IC_{50}$ for compounds C3 and C4 was 5 µM. As C2 was toxic for Cos1 cells, its effect on aggregation was not determined.

The protein levels of Htt fragments containing 103Q in PC12 cells were not affected by incubation with compounds at the concentrations tested. Furthermore, proteolytic capacity of cells treated with compound C2 appeared to be normal, since levels of a highly unstable endogenous p53 protein in PC12 cells were not changed. Together, these data suggest that inhibition of aggregate formation by C2 was not related to general inhibition of cell viability, general cessation of metabolism or an increase in the cells' general capacity to degrade or refold abnormal proteins.

To determine whether C2 could directly interfere with polyQ aggregation, we reproduced this process in vitro and assayed the inhibitory effects of the compounds in a cell-free trap assay. Recombinant HD Q51 polypeptide, purified from bacteria, was incubated in the presence or in the absence of C2 for a time sufficient to allow aggregation. Then, upon heat-denaturation in SDS buffer, samples were filtered through a cellulose acetate membrane. Harsh denaturation conditions separated unaggregated soluble peptides, which passed through the membrane, and insoluble aggregates, which were retained on the membrane. The polyQ aggregates trapped on the membrane were subsequently immunostained and quantified. The compound failed to block aggregation of pure polyglutamines in vitro even at high concentrations (up to 100 mM). These data suggest that the molecular targets of these compounds were not soluble or aggregated polyQ.

Suppression of aggregation of 103Q could be related to potential induction of heat shock proteins that facilitate folding and degradation of abnormal polypeptides. However, the compounds failed to affect expression of the major inducible heat shock protein, Hsp72, indicating that expression of Hsps is not regulated by the tested compounds in PC12 cells.

To devise more potent inhibitors of polyQ aggregation, we assembled a focus library consisting of chemical compounds having more than 70% structural similarity to C1-C4. We tested these analogs at concentrations ranging from 0.025 μM to 5.0 μM for their effects on polyQ aggregation in PC12 cells. Among 24 analogs of C1; 28 analogs of C2; 24 analogs of C3, and 53 analogs of C4, we identified several potent inhibitors of polyQ aggregation. From our C2 focus library, we isolated compound C2-8 (B2 in Table 2), which inhibits polyQ aggregation with an $IC_{50}$ value 50 nM. We also identified C2-10 (B6 in Table 2) and C2-11 (M16 (formula V(n)) in Table 5), and B7, B8 and B9 in Table 2. From our C3 focus library, we isolated compound C3-5 (M22 (formula V(t)) in Table 5) (having an $IC_{50}$ value of 100 nM) and compound C3-6 (M17 (formula V(o)) in Table 5) (having an $IC_{50}$ value of 5 μM). From our C4 library, we isolated compound C4-7 (A31 in Table 1), which has an $IC_{50}$ value 100 nM. We also identified C4-34 (A3 in Table 1).

The compounds demonstrated no effects on expression levels of 103Q polypeptides and no toxicity at the concentrations used to inhibit aggregation. In the C1 library, no inhibitors of polyQ aggregation with high potency were found. The original "hit" compounds C1-C4 and their structural analogs displayed specificity in inhibiting aggregation. Although these compounds were potent inhibitors of polyQ aggregation, they failed to inhibit alpha-synuclein aggregation in preliminary tests in a cellular model of Parkinson's disease.

The effects of the selected compounds on polyQ aggregation in neuronal tissues were assessed in brain slice cultures from the transgenic mouse R6/2 model of HD. R6/2 mice ubiquitously express human Huntingtin exon I containing 150Q (HD Q150), which causes neuropathology resembling key neurological changes in HD patients. Formation of neuronal polyQ aggregates precedes pathological behavioural changes in R6/2 mice. An organotypic slice culture assay has been developed in order to establish an ex vivo system that closely models the process of aggregation occurring in R6/2 mouse brains. The early appearance of polyQ aggregates in the R6/2 mouse hippocampus makes it an ideal model to test aggregation inhibitors in an ex vivo system: aggregates appear in neurons in the slice cultures at the same time they appear in neurons in intact brains of transgenic mice. The potency of any aggregate inhibitor can be assessed directly in neurons in brain slices (thus bypassing the blood brain barrier, the major obstacle to test compounds in neuronal tissues).

Aggregation in brain slice cultures was assessed during four weeks using three parameters: (1) the number of aggregates per square millimeter, (2) the density of individual aggregates, and (3) the size of the aggregates. These parameters can be assessed in any of the assays described herein. Brain slices maintained in culture for 2, 3 or 4 weeks were fixed and immunostained using an anti-Htt-antibody. Fluorescent images of aggregates were captured as Z stacks using a Confocal Microscope, capturing aggregates throughout the entire thickness of the slice. To obtain statistically significant data, 20 sections for each sample were quantified with a macro computer program (Paul Wetton at Image Associates, UK), which measured aggregate count, aggregate density and aggregate size.

The test compounds were added to the slice cultures from Day 1 in regular media, which were changed twice a week. The four hit-compounds, C1-C4, were tested at concentrations of 0.1 mM, 1 mM, 10 mM and 100 mM. The five structural analogues, C5-C9 (C5 is in M15 in Table 5; C6 is M14 in Table 5; C7 is A2 in Table 1; C8 is B2 in Table 2; C9 is A33 in Table 1), were tested at concentrations 0.001 mM, 0.01 mM, 0.1 mM, 1 mM and 10 mM.

The inhibitory effects on aggregation of primary hit-compounds were restricted to 2-3 weeks in brain slice culture at 0.1-10 μM concentrations. At higher concentrations of 10-100 μM, these compounds were toxic for neurons.

To date, the most successful inhibitor identified by this screen was C2-8 (B2 in Table 2). At the 3-week time point, aggregates intensity and area was inhibited only by the highest tested concentration of 10 mM. After 4 weeks of incubation with C2-8, inhibition occurred at concentrations ranging from 0.1-10 mM for every parameter assayed, but 10 mM showed the strongest effect.

Compound C2-8 was also tested in a cell-free trap assay of purified polyQ, and showed inhibitory effects on aggregation, albeit at very high concentrations ($IC_{50}$ 25 μM). Congo Red, which is structurally unrelated to C2-8, was used as a control. Our data suggested that either C2-8 is metabolically converted by cells into a highly potent inhibitor or that it affected cellular factors involved in regulation of protein aggregation.

Example 7

Naphthylamine Scaffold Compounds

Previous studies for drugs to treat HD identified naphthylamine scaffold compounds. Compounds from this chemical class were identified as inhibitors of polyglutamine aggregation and transcriptional regulators. The compounds include HDAc inhibitors such as scriptaid, DAc inhibitors, DNA intercalation agents, inhibitors of topoisomerase II, and the anticancer drugs amonofide and mitonafide.

A variety of animal models of Huntington disease have been developed. Examination of the degeneration of photoreceptor neurons facilitated by extended polyQ expression is one such model (Jackson et al., Neuron 21:633-642, 1998).

We used the photoreceptor model in Drosophila to test a variety of different compounds, including naphthylamine derivatives, for an effect on neurodegeneration. One naphthylamine analog, C9-2 (A8 in Table 1), showed dramatic neuroprotection. C9-2 is 2-(3-methoxypropyl)-1H-benzo[de]isoquinoline-1,3(2H)-dione.

Biochemical activity associated with C9-2 is not well understood. The compound is structurally similar to scriptaid, but unlike scriptaid, C9-2 does not appear to inhibit HDAc activity. Further, no transcriptional activation or repression was observed when C9-2 was tested in the striatum of 11Q/111Q cells and PC12 cells, nor has DNA binding activity been detected. C9-2 also does not appear to suppress aggregation of polyQ-containing polypeptides. Future studies include testing the compound for anti-apoptotic activity, and transcriptional profiling using a striatum cell line derived from a double knock-out mutant htt mouse. The C9-2 analogs C9-2B (A30 in Table 1) and C9-2A (control) (A29 in Table 1) are being tested for an effect on photoreceptor neurodegeneration in the Drosophila HD model.

Example 8

Transcriptional Dysregulation

Transcriptional dysregulation is a hallmark of HD. Regulators of global transcription, including HDAc inhibitors, have been shown to ameliorate disease pathology. We found that the compound C9 could repress transcription in PC12 cells expressing a polypeptide with an extended polyQ (103Q) N-terminal fragment. Expression of the polypeptide was under control of an inducible ecdysone receptor (EcR)-based promoter.

We then tested C9 in chromatin immunoprecipitation (ChIP) assays. Such assays are useful for measuring binding of transcriptional factors and histones to DNA. It was previously demonstrated that cells derived from striatum of double knock-in mutant (111Q) full-length htt mice are deficient in binding of the transcription factor SP1 to dopamine receptor (D2) DNA. The compound C9 was found to restore binding of SP1 and increase binding of histones (and acetylated histones in particular) to D2 DNA. The compound also demonstrated unspecific toxicity to cells at concentrations higher than 10 µM.

C9 was tested in the HD *Drosophila* model and showed modest rescue of neurodegeneration of photoreceptor neurons.

Mouse trials were also conducted with C9, and while the compound was found to be bioavailable, an effect was not observed, presumably due to low potency of the compound. Scriptaid was toxic to flies.

We conducted structure activity relationship (SAR) studies to optimize transcription activation. We developed a novel transcription-based assay for this purpose. A luciferase reporter gene was stably integrated into 111Q/111Q striatum double knock-in cells and constitutively expressed under control of a promoter containing six copies of the SP1 trancription factor binding motif (6XSP1). In this system, C9 was determined to have an $EC_{200}$ of 7.5 µM. This result is similar to the transcription activation efficacy observed for scriptaid. C9 was also found to activate transcription in the neuronal cell line H4.

A series of C9 derivatives were designed, synthesized, and tested in the ChIP and transcription-based assays described above. The analog C91 (A9 in Table 1) was more potent (4 µM) than C9, and exhibited a similar result in ChIP experiments. C9-2 and C9-3 (A7 in Table 1) did not effectively activate transcription. Compound C9-1B (A14 in Table 1) was even more potent than C9 and C91, with an $EC_{200}$ of 50 nM. This compond also demonstrated some weak nonspecific toxicity in the range of 1.25-5.0 µM. The compounds tested generally demonstrated the best response 72 hours after exposing the cells to the chemicals. This result contrasts with that of the HDAc inhibitors which demonstrate a peak transcriptional response in the transcription assay at 24 hours following exposure of cells to compounds. The delay in the response in the C9 compounds suggests that the mechanism of transcriptional activation is different than that of the HDAc inhibitors. The delayed response also indicates that the compounds are generally stable in the cellular environment.

In the course of the SAR study, we also identified structures that had previously been developed as cancer drugs, such as the naphthalimides, mitonafide and amonafide (C91CN and C91C, respectively). These compounds are known to be DNA intercalators with antitumor activity. Testing of the DNA-binding activity of the C9 compounds revealed no correlation between constant DNA binding and transcriptional response. This is in contrast to the effect of mithramycin which binds DNA and was shown to be highly efficacious in a mouse HD model (Ferrante et al., *Soc Neurosci Abstr* 28: 725, 2002b). Mithramycin potently activated transcription in our assay. Similar to many anti-tumor compounds, mithramycin is toxic to cells. The C9 series lead compounds, however, do not show a similar toxicity.

Compounds of the C9 series did not directly inhibit HDAc activity, but C9-4 (A19 in Table 1) demonstrated indirect HDAc inhibitory activity at high concentrations, targeting down-regulation of HDAc 5 specifically. Thus, the C9 compounds may modulate transcriptional activity by an indirect effect on the HDAc pathway.

C9-1B and C9-6B (C9-1B is A14 in Table 1; C9-6B is A23 in Table 1) will be tested in a mouse model of HD.

A series of rationally-designed scaffold-type compounds, called the CG series of compounds, was tested in the transcription assay described above. CG4 (A27 in Table 1) was the most potent transcriptional activator, but was less potent than C9-4.

Example 9

Screening of Chemical Compound Libraries

A PC12 cell line was engineered to express extended polyQ under the control of an ecdysone-inducible promoter. In the assay cell line, an N-terminal fragment of htt containing an extended polyQ tract was stably expressed as a fusion with EGFP (htt103Q-EGFP), from the pIND vector. Expression of extended polyQ in these cells was controlled by addition of an ecdysone analog, in this case muristerone A. In this assay, EGFP fluorescence directly correlated with htt103Q-EGFP expression levels. This system was designed to assess the effects of specific compounds on overall levels of extended polyglutamines in cells, using a simple fluorescent-based read-out.

Using this assay, several compounds were identified as facilitators of protein aggregation. These compounds are D1, D2, and D3, shown in Table 4. PC12 cells expressing the extended polyQ polypeptide exhibited proteasomal dysfunction, and compounds D1 and D2 relieved this phenotype. The compound D4 was found to inhibit protein aggregation.

The contents of U.S. Ser. No. 60/630,252, filed on Nov. 22, 2004; U.S. Ser. No. 60/630,231, filed on Nov. 22, 2004; U.S. Ser. No. 60/630,221, filed on Nov. 22, 2004; U.S. Ser. No. 60/630,262, filed on Nov. 22, 2004; U.S. Ser. No. 60/630,230, filed on Nov. 22, 2004; and U.S. Ser. No. 60/633,478, filed on Dec. 6, 2004 are each hereby incorporated by reference in the present application.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a subject who has been diagnosed as having, or who is at risk of developing, Huntington's Disease, the method comprising identifying the subject and administering to a subject in need thereof a therapeutically effective amount of a pharmaceutical composition comprising a compound of Formula II:

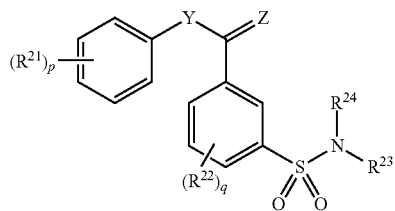

Formula II wherein
- Z is O or S;
- Y is O, $NR^{25}$ or $CR^{26}R^{27}$;
- $R^{21}$ is halo or hydroxy;
- $R^{22}$ is nitro, cyano, amino, amido, or alkyl;
- $R^{23}$ is aryl substituted with halo, nitro, cyano, amino, amido, or alkyl;
- $R^{24}$ is H or alkyl;
- $R^{25}$ is H or alkyl;
- each $R^{26}$ and $R^{27}$ is independently H or alkyl;
- each p and q are independently an integer from 0-4, and a pharmaceutically acceptable carrier.

2. The method of claim 1, wherein Z is O.
3. The method of claim 1, wherein Y is $NR^{25}$.
4. The method of claim 1, wherein $R^{25}$ is H.
5. The method of claim 1, wherein $R^{21}$ is bromo.
6. The method of claim 1, wherein the pharmaceutical composition comprises:
   N-(4-Bromo-phenyl)-3-(4-bromo-phenylsulfamoyl)-benzamide; or
   3-(4-Bromo-phenylsulfamoyl)-N-phenyl-benzamide.

7. A method of treating a subject who has been diagnosed as having Parkinson's Disease, the method comprising identifying the subject and administering to a subject in need thereof a therapeutically effective amount of a pharmaceutical composition comprising a compound of Formula II:

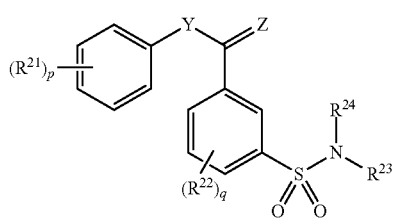

Formula II wherein,
- Z is O or S;
- Y is O, $NR^{25}$ or $CR^{26}R^{27}$;
- $R^{21}$ is halo or hydroxy;
- $R^{22}$ is nitro, cyano, amino, amido, or alkyl;
- $R^{23}$ is aryl substituted with halo, nitro, cyano, amino, amido, or alkyl;
- $R^{24}$ is H or alkyl;
- $R^{25}$ is H or alkyl;
- each $R^{26}$ and $R^{27}$ is independently H or alkyl;
- each p and q are independently an integer from 0-4, and a pharmaceutically acceptable carrier.

8. The method of claim 7, wherein Z is O.
9. The method of claim 7, wherein Y is $NR^{25}$.
10. The method of claim 7, wherein $R^{25}$ is H.
11. The method of claim 7, wherein $R^{21}$ is bromo.
12. The method of claim 7, wherein the pharmaceutical composition comprises:
    N-(4-Bromo-phenyl)-3-(4-bromo-phenylsulfamoyl)-benzamide; or
    3-(4-Bromo-phenylsulfamoyl)-N-phenyl-benzamide.

* * * * *

UNITED STATES PATENT AND TRADEMARK OFFICE
CERTIFICATE OF CORRECTION

| | |
|---|---|
| PATENT NO. | : 8,404,747 B2 |
| APPLICATION NO. | : 11/076093 |
| DATED | : March 26, 2013 |
| INVENTOR(S) | : Aleksey G. Kazantsev et al. |

It is certified that error appears in the above-identified patent and that said Letters Patent is hereby corrected as shown below:

On the Title Page and Page 2, Column 1 (Related U.S. Application Data), lines 1-5 (First Page) and 1-6 (Page 2), delete "Provisional application No. 60/550,748, filed on Mar. 5, 2004, provisional application No. 60/630,221, filed on Nov. 22, 2004, provisional application No. 60/630,230, filed on Nov. 22, 2004, provisional application No. 60/630,231, filed on Nov. 22, 2004, provisional application No. 60/630,252, filed on November 22, 2004, provisional application No. 60/630,262, filed on Nov. 22, 2004, provisional application No. 60/630,264, filed on Nov. 22, 2004, provisional application No. 60/633,487, filed on Dec. 6, 2004." and insert -- Provisional application No. 60/550,748, filed on Mar. 5, 2004, provisional application No. 60/630,264, filed on Nov. 22, 2004. --.

Signed and Sealed this
Third Day of September, 2013

Teresa Stanek Rea
*Acting Director of the United States Patent and Trademark Office*